United States Patent
Meissner et al.

(10) Patent No.: US 7,186,838 B2
(45) Date of Patent: Mar. 6, 2007

(54) FLUORINATED 4-AZASTEROID DERIVATIVES AS ANDROGEN RECEPTOR MODULATORS

(75) Inventors: Robert S. Meissner, Schwenksville, PA (US); James J. Perkins, Churchville, PA (US)

(73) Assignee: Merck & Co., Inc., Rahway, NJ (US)

( * ) Notice: Subject to any disclaimer, the term of this patent is extended or adjusted under 35 U.S.C. 154(b) by 195 days.

(21) Appl. No.: 10/507,239

(22) PCT Filed: Mar. 7, 2003

(86) PCT No.: PCT/US03/08277

§ 371 (c)(1),
(2), (4) Date: Sep. 9, 2004

(87) PCT Pub. No.: WO03/077919

PCT Pub. Date: Sep. 25, 2003

(65) Prior Publication Data

US 2005/0165039 A1    Jul. 28, 2005

(51) Int. Cl.
*C07D 221/18*    (2006.01)
*C07D 401/12*    (2006.01)
(52) U.S. Cl. .......................... 546/77; 546/61
(58) Field of Classification Search ................ 546/77, 546/61
See application file for complete search history.

(56) References Cited

U.S. PATENT DOCUMENTS 5,187,278 A    2/1993    King et al.

OTHER PUBLICATIONS

Rasmusson G.H., et al. "Azasteroids: Structure Activity Relationships for Inhibition of 5 alpha-Reductase and of Androgen Receptor Binding", J. Med. Chem, vol. 29, pp. 2298-2315 (1986).
Brooks J.R., et al. "5 alpha-Reductase Inhibitory and Anti-Androgenic Activities of Some 4-Azasteroids in the Rat", Steroids, vol. 47, pp. 1-19 (1986).

*Primary Examiner*—Charanjit S. Aulakh
(74) *Attorney, Agent, or Firm*—Patricia A. Shatynski; Mark R. Daniel

(57) ABSTRACT

Compounds of structural formula I are modulators of the androgen receptor (AR) in a tissue selective manner. They are useful as agonists of the androgen receptor in bone and/or muscle tissue while antagonizing the AR in the prostate of a male patient or in the uterus of a female patient. These compounds are therefore useful in the treatment of conditions caused by androgen deficiency or which can be ameliorated by androgen administration, including osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, inflammatory arthritis and joint repair, HIV-wasting, prostate cancer, cancer cachexia, muscular dystrophies, premature ovarian failure, and autoimmune disease, alone or in combination with other active agents.

25 Claims, No Drawings

FLUORINATED 4-AZASTEROID DERIVATIVES AS ANDROGEN RECEPTOR MODULATORS

FIELD OF THE INVENTION

The present invention relates to fluorinated 4-azasteroid derivatives, their synthesis, and their use as androgen receptor modulators. More particularly, the compounds of the present invention are tissue-selective androgen receptor modulators and are thereby useful for the treatment of conditions caused by androgen deficiency or which can be ameliorated by androgen administration, such as osteoporosis, periodontal disease, bone fracture, frailty, and sarcopenia.

BACKGROUND OF THE INVENTION

The androgen receptor (AR) belongs to the superfamily of steroid/thyroid hormone nuclear receptors, whose other members include the estrogen receptor (ER), the progesterone receptor (PR), the glucocorticoid receptor (GR), and the mineralocorticoid receptor (MR). The AR is expressed in numerous tissues of the body and is the receptor through which the physiological as well as the pathophysiological effects of endogenous androgen ligands, such as testosterone (T) and dihydrotestosterone (DHT), are expressed. Structurally, the AR is composed of three main functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist.

Androgen ligand binding to the AR affords a ligand/receptor complex, which, subsequent to translocation inside the nucleus of the cell, binds to specific regulatory DNA sequences (referred to as androgen response elements or AREs) within the promoter or enhancer regions of the target gene or genes present in the cell's nucleus. Other proteins termed cofactors are next recruited which bind to the amino-terminal domain or the LBD of the receptor leading to gene transcription and subsequent translation to produce the protein(s) encoded by that gene or genes.

Androgen therapy has been used in the clinic to treat a variety of male disorders, such as reproductive disorders and primary or secondary male hypogonadism. Moreover, a number of natural or synthetic AR agonists have been clinically investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, have been used to treat prostate cancer. It would therefore be useful to have available compounds that can activate ("agonize") the function of the AR in a tissue-selective manner which would afford the desired beneficial osteo- and myoanabolic effects of androgens but without the negative androgenic properties, such as virilization and induction of an atherogenic lipid profile which can lead to cardiovascular disease.

The role of androgens in bone formation has been documented. For example, anabolic steroids, such as nandrolone decanoate or stanozolol, have been shown to increase bone mass in postmenopausal women. The beneficial effects of androgens on bone in postmenopausal osteoporosis were documented in recent studies using combined testosterone and estrogen administration [Hofbauer, et al., "Androgen effects on bone metabolism: recent progress and controversies," *Eur. J. Endocrinol.* 140: 271–2.86 (1999)]. Combined treatment significantly increased, the rate and extent of the rise in bone mineral density (BMD) in the lumbar and hip regions, relative to treatment with estrogen alone. Additionally, estrogen—progestin combinations that incorporated an androgenic progestin (such as norethindrone), rather than medroxyprogesterone acetate, yielded greater improvements in hip BMD. These results have recently been confirmed in a larger 2-year, double-blind comparison study in which oral conjugated estrogen (CEE) and methyltestosterone combinations were demonstrated to be effective in promoting accrual of bone mass in the spine and hip, while conjugated estrogen therapy alone prevented bone loss ["A two-year, double-blind comparison of estrogen-androgen and conjugated estrogens in surgically menopausal women: Effects on bone mineral density, symptoms and lipid profiles," *J. Reprod. Med.*, 44: 1012–1020 (1999)]. Despite the beneficial effects of androgens in postmenopausal women, the use of androgens has been limited because of the undesirable virilizing and metabolic action of androgens. The data from Watts and colleagues demonstrate that hot flushes decrease in women treated with CEE and methyltestosterone; however, 30% of these women suffered from significant increases in acne and facial hair, a complication of all current androgen pharmacotherapies [Watts, et al., "Comparison of oral estrogens and estrogens plus androgen on bone mineral density, menopausal symptoms, and lipid-lipoprotein profiles in surgical menopause," *Obstet. Gynecol.*, 85: 529–537 (1995)]. Moreover, the addition of methyltestosterone to CEE markedly decreased HDL levels, as seen in other studies. Therefore, non-tissue selective AR agonists may increase the risk of cardiovascular disease. Thus, the virilizing potential and negative effects on lipid profile of current androgen therapies provide a strong rationale for developing tissue-selective androgen receptor agonists for bone. Reference is made to J. A. Kanis, "Other agents for generalized osteoporosis," in *Osteoporosis*, Blackwell Science, Ch. 8, pp 196–227 (1994) for a discussion of non-selective anabolic steroids in the treatment of osteoporosis.

It is also well established that androgens play an important role in bone metabolism in men, which parallels the role of estrogens in women [Anderson, et al., "Androgen supplementation in eugonadal men with osteoporosis—effects of six months of treatment on bone mineral density and cardiovascular risk factors," *Bone*, 18: 171–177 (1996)]. Even in eugonadal men with established osteoporosis, the therapeutic response to testosterone treatment provided additional evidence that androgens exert important osteoanabolic effects. Mean lumbar BMD increased from 0.799 gm/cm$^2$ to 0.839 g/cm$^2$, in 5 to 6 months in response to 250 mg of testosterone ester administered intramuscularly every fortnight. A common scenario for androgen deficiency occurs in men with stage D prostate cancer (metastatic) who undergo androgen deprivation therapy (ADT). Endocrine orchiectomy is achieved by long acting GnRH agonists, while androgen receptor blockade is implemented with flutamide, nilutamide, bicalutamide, or RU 58841 (AR antagonists). In response to hormonal deprivation, these men suffered from hot flushes, significant bone loss, weakness, and fatigue. In a recent pilot study of men with stage D prostate cancer, osteopenia (50% vs. 38%) and osteoporosis (38% vs. 25%) were more common in men who had undergone ADT for greater than one year than the patients who did not undergo ADT [Wei, et al., "Androgen deprivation therapy for prostate cancer results in significant loss of bone density," *Urology*, 54: 607–611 (1999)]. Lumbar spine BMD was significantly lower in men who had undergone ADT. Thus, in addition to the use of tissue selective AR agonists for osteoporosis, tissue selective AR antagonists in the prostate that lack antagonistic action in bone and muscle may be useful agents for the treatment of prostate cancer, either alone or as an adjunct to traditional ADT such as with a GnRH agonist/antagonist [See also A. Stoch, et al., *J. Clin. Endocrin. Metab.*, 86: 2787–2791 (2001)]. Tissue-selective AR antagonists may also have utility in the treatment of polycystic ovarian syndrome in postmenopausal women [see C. A. Eagleson, et al., "Polycystic ovarian syndrome: evidence that flutamide restores sensitivity of the gonadotropin-releasing hormone pulse generator to inhibition by estradiol and progesterone," *J. Clin. Endocrinol. Metab.*, 85: 4047–4052 (2000) and E. Diamanti-Kandarakis, "The Effect of a Pure Antiandrogen Receptor Blocker, Flutamide, on the Lipid Profile in the Polycystic Ovary Syndrome," *Int. J. Endocrinol. Metab.*, 83: 2699–2705 (1998).

There is a need for more effective agents to treat osteopenia and osteoporosis in both men and women. Osteoporosis is characterized by bone loss, resulting from an imbalance between bone resorption (destruction) and bone formation, which starts in the fourth decade and continues throughout life at the rate of about 1–4% per year [Eastell, "Treatment of postmenopausal osteoporosis," *New Engl. J. Med.*, 338: 736 (1998)]. In the United States, there are currently about 20 million people with detectable fractures of the vertebrae due to osteoporosis. In addition, there are about 250,000 hip fractures per year due to osteoporosis, associated with a 12%–20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs), and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site, higher in the trabecular bone of the vertebrae than in the cortex of the long bones, the bone resorption inhibitors are less effective in increasing hip BMD and preventing hip fracture. Therefore, osteoanabolic agents, which increase cortical bone formation and bone mass of long bones by stimulating periosteal bone formation, would address an unmet need in the treatment of osteoporosis especially for patients with high risk of hip fractures. The osteoanabolic agents also complement the bone resorption inhibitors that target the trabecular envelope, leading to a biomechanically favorable bone structure (Schmidt, et al., "Anabolic steroid: Steroid effects on bone in women," In: J. P. Bilezikian, et al., Ed., *Principles of Bone Biology*, San Diego: Academic Press, 1996). Tissue-selective AR agonists with diminished deleterious effects on the cardiovascular system and limited virilizing potential may be useful as a monotherapy for the prevention and/or treatment of female osteoporosis. In addition, a compound with osteoanabolic properties in bone and muscle but with reduced activity in the prostate and sex accessory tissues may be useful for the prevention and/or treatment of male osteoporosis and osteopenia in men, particularly elderly men.

Selective androgen receptor modulators may also be useful to treat certain hematopoietic disorders. It is known that androgens stimulate renal hypertrophy and erythropoietin (EPO) production. Prior to the introduction of recombinant human EPO, androgens were employed to treat anemia caused by chronic renal failure. In addition, androgens at pharmacological doses were found to increase serum EPO levels in anemic patients with non-severe aplastic anemia and myelodysplastic syndromes but not in non-anemic patients. Treatment modalities for anemia will require selective action such as may be provided by selective androgen receptor modulators.

Furthermore, selective androgen receptor modulators may also have clinical value as an adjunct to the treatment of obesity. This approach to lowering body fat is supported by published observations that androgen administration reduced subcutaneous and visceral abdominal fat in obese men [J. C. Lovejoy, et al., "Oral anabolic steroid treatment, but not parenteral androgen treatment, decreases abdominal fat in obese, older men," Int. *J. Obesity*, 19: 614–624 (1995)]. Therefore, SARMs devoid of androgenic effects on prostate may be beneficial in the treatment of obese men. In a separate study, androgen administration resulted in loss of subcutaneous abdominal fat in obese postmenopausal women [J. C. Lovejoy, et al., "Exogenous Androgens Influence Body Composition and Regional Body Fat Distribution in Obese Postmenopausal Women—A Clinical Research Center Study," *J. Clin. Endocrinol. Metab.*, 81: 2198–2203 (1996)]. In the latter study, nandroldne decanoate, a weak androgen and anabolic agent, was found to increase lean body mass and resting metabolic rate in obese postmenopausal women consuming a weight-reducing diet.

Non-steroidal compounds having androgen receptor modulating properties were disclosed in U.S. Pat. Nos. 5,688,808; 5,696,130; 6,017,924; 6,093,821; WO 01/16139 (published 8 Mar. 2001); and WO 01/16108 (published 8 Mar. 2001), all assigned to Ligand Pharmaceuticals, and in WO 01/27086, assigned to Kaken Pharm. Co. Additional background for the rationale behind the development of Selective Androgen Receptor Modulators is found in L. Zhi and E. Martinborough in *Ann. Rep. Med. Chem.* 36: 169–180 (2001). Non-steroidal SARMs were disclosed in J. P. Edwards, "New Nonsteroidal Androgen Receptor Modulators Based on 4-(Trifluoromethyl)-2(1H)-Pyrrolidino[3,2-g] quinolinone," *Bioorg. Med. Chem. Lett.*, 8: 745–750 (1998) and in L. Zhi et al., "Switching Androgen Receptor Antagonists to Agonists by Modifying C-ring Substituents on Piperidino[3,4-g]quinolinone," *Bioorg. Med. Chem. Lett.*, 9: 1009–1012 (1999).

There exists a need in the clinical art for more effective agents that can elicit the positive responses of androgen replacement therapy but without the undesired side effects of non-tissue selective agonists of the AR. What is needed are compounds that can produce the same positive responses as androgen replacement therapy but without the undesired side effects. Also needed are androgenic compounds that exert selective effects on different tissues of the body. In this invention, we have identified compounds that function as selective androgen receptor modulators (SARMs) using a series of in vitro cell-assays that profile ligand mediated activation of AR, such as (i) N—C interaction, (ii) transcriptional repression, and (iii) transcriptional activation. SARM compounds in this invention, identified with the methods listed above, exhibit tissue selective AR agonism in vivo, i.e.

agonism in bone (stimulation of bone formation in a rodent model of osteoporosis) and antagonism in prostate (minimal effects on prostate growth in castrated rodents and antagonism of prostate growth induced by AR agonists).

The compounds of the present invention identified as SARMs are useful to treat diseases or conditions caused by androgen deficiency which can be ameliorated by androgen administration. Such compounds are ideal for the treatment of osteoporosis in women and men as a monotherapy or in combination with inhibitors of bone resorption, such as bisphosphonates, estrogens, SERMs, cathepsin K inhibitors, αvβ3 integrin receptor antagonists, calcitonin, and proton pump inhibitors. They can also be used with agents that stimulate bone formation, such as parathyroid hormone or analogs thereof. The SARM compounds of the present invention may also be employed for treatment of prostate disease, such as prostate cancer and benign prostatic hyperplasia (BPH). Moreover, compounds of this invention exhibit minimal effects on skin (acne and facial hair growth) and may be useful for treatment of hirsutism. Additionally, compounds of this invention can stimulate muscle growth and may be useful for treatment of sarcopenia and frailty. They can be employed to reduce subcutaneous and visceral abdominal fat in the treatment of obesity. Moreover, compounds of this invention can exhibit androgen agonism in the central nervous system and may be useful to treat vasomotor symptoms (hot flush) and to increase energy and libido, particularly in postmenopausal women. The compounds of the present invention may be used in the treatment of prostate cancer, either alone or as an adjunct to traditional GnRH agonist/antagonist therapy, for their ability to restore bone, or as a replacement for antiandrogen therapy because of their ability to antagonize androgen in the prostate, and minimize bone depletion in the skeletal system. Further, the compounds of the present invention may be used for their ability to restore bone in the treatment of pancreatic cancer as an adjunct to treatment with antiandrogen, or as monotherapy for their antiandrogenic properties, offering the advantage over traditional antiandrogens of being bone-sparing. Additionally, compounds of this invention can increase the number of blood cells, such as red blood cells and platelets, and may be useful for the treatment of hematopoietic disorders, such as aplastic anemia. Finally, compounds of this invention have minimal effects on lipid metabolism. Thus, considering their tissue selective androgen receptor agonism listed above, the compounds of this invention are ideal for hormone replacement therapy in hypogonadic (androgen deficient) men.

It is therefore an object of the present invention to provide fluorinated 4-azasteroid derivatives which are useful as selective androgen receptor modulators.

It is another object of the present invention to provide pharmaceutical compositions comprising the fluorinated 4-azasteroid derivatives of the present invention in association with a pharmaceutically acceptable carrier.

It is another object of the present invention to provide pharmaceutical compositions comprising the fluorinated 4-azasteroid derivatives for use as selective androgen receptor modulators.

It is another object of the present invention to provide methods for the treatment of diseases or conditions caused by androgen deficiency which can be ameliorated by androgen administration.

It is another object of the present invention to provide methods for the treatment of diseases or conditions caused by androgen deficiency which can be ameliorated by androgen administration in combination with other agents.

It is another object of the present invention to provide fluorinated 4-azasteroid derivatives and their pharmaceutical compositions for use as a medicament for the treatment of diseases or conditions caused by androgen deficiency which can be ameliorated by androgen administration.

It is another object of the present invention to provide fluorinated 4-azasteroid derivatives and their pharmaceutical compositions for the manufacture of a medicament for the treatment of diseases or conditions caused by androgen deficiency which can be ameliorated by androgen administration.

These and other objects will become readily apparent from the detailed description which follows.

SUMMARY OF THE INVENTION

The present invention relates to compounds of structural formula I:

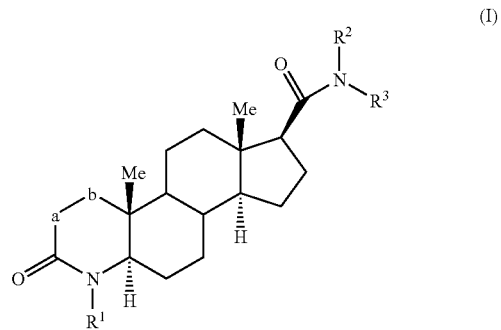

or a pharmaceutically acceptable salt or an enantiomer thereof; wherein n is 0, 1 or 2;

a-b represents CF=CH, CHFCH$_2$, or CF$_2$CH$_2$;

R$^1$ is hydrogen, hydroxymethyl, or C$_{1-3}$ alkyl, wherein alkyl is unsubstituted or substituted with one to seven fluorine atoms;

R$^2$ is hydrogen or C$_{1-4}$ alkyl;

R$^3$ is selected from
  C$_{1-4}$ alkyl,
  (CH$_2$)$_n$-cycloheteroalkyl, and
  (CH$_2$)$_n$-aryl, wherein aryl is selected from
    (1) phenyl,
    (2) naphthyl,
    (3) benzimidazolyl,
    (4) benzofuranyl,
    (5) benzothiophenyl,
    (6) benzoxazolyl,
    (7) benzothiazolyl,
    (8) benzodihydrofuranyl,
    (9) 1,3-benzodioxolyl,
    (10) 2,3-dihydro-1,4-benzodioxinyl,
    (11) indolyl,
    (12) quinolyl,
    (13) isoquinolyl,
    (14) furanyl,
    (15) thienyl,
    (16) imidazolyl,
    (17) oxazolyl,
    (18) thiazolyl,
    (19) isoxazolyl,
    (20) isothiazolyl,

(21) pyrazolyl,
(22) pyrrolyl,
(23) pyridyl,
(24) pyrimidyl,
(25) pyrazinyl,
(26) thiadiazolyl,
(27) oxadiazolyl,
(28) triazolyl,
(29) tetrazolyl, and
(30) indanyl;

wherein the alkyl group or the cycloheteroalkyl group is unsubstituted or substituted with one to three substituents independently selected from halogen, hydroxy, and $C_{1-4}$ alkoxy; the aryl group as defined in items (1) to (30) is unsubstituted or substituted with one to three groups independently selected from halogen, phenyl, $C_{1-8}$ alkyl, $C_{3-8}$ cycloalkyl, $C_{3-8}$ cycloheteroalkyl, phenyl-$C_{1-6}$ alkyl, amino-$C_{0-6}$ alkyl, $C_{1-6}$ alkylamino-$C_{0-6}$ alkyl, ($C_{1-6}$ alkyl)$_2$amino-$C_{0-6}$ alkyl, phenyl-$C_{0-6}$ alkylamino-$C_{0-6}$ alkyl, (phenyl-$C_{0-6}$ alkyl)$_2$amino-$C_{0-6}$ alkyl, $C_{1-6}$ alkylthio, phenyl-$C_{0-6}$ alkylthio, $C_{1-6}$ alkylsulfinyl, phenyl-$C_{0-6}$ alkylsulfinyl, $C_{1-6}$ alkylsulfonyl, phenyl-$C_{1-6}$ alkylsulfonyl, $C_{1-6}$ alkoxy-$C_{0-6}$ alkyl, phenyl-$C_{0-6}$ alkoxy-$C_{0-6}$ alkyl, hydroxycarbonyl-$C_{0-6}$ alkyl, $C_{1-6}$ alkoxycarbonyl-$C_{0-6}$ alkyl, phenyl-$C_{0-6}$ alkoxycarbonyl-$C_{0-6}$ alkyl, hydroxycarbonyl-$C_{1-6}$ alkyloxy, hydroxy-$C_{0-6}$ alkyl, cyano, nitro, perfluoro-$C_{1-4}$ alkyl, perfluoro-$C_{1-4}$ alkoxy, oxo, $C_{1-6}$ alkylcarbonyloxy, phenyl-$C_{0-6}$ alkylcarbonyloxy, $C_{1-6}$ alkylcarbonylamino, phenyl-$C_{0-6}$ alkylcarbonylamino, $C_{1-6}$ alkylsulfonylamino, phenyl-$C_{0-6}$ alkylsulfonylamino, $C_{1-6}$ alkoxycarbonylamino, phenyl-$C_{0-6}$ alkoxycarbonylamino, $C_{1-6}$ alkylaminocarbonylamino, phenyl-$C_{0-6}$ alkylaminocarbonylamino, ($C_{1-6}$ alkyl)$_2$ aminocarbonylamino, (phenyl-$C_{0-6}$ alkyl)$_2$ aminocarbonylamino, ($C_{1-6}$ alkyl)$_2$ aminocarbonyloxy, and (phenyl-$C_{0-6}$ alkyl)$_2$ aminocarbonyloxy; and wherein any methylene (CH$_2$) carbon atom in (CH$_2$)$_n$ is unsubstituted or substituted with one to two groups independently selected from halogen, hydroxy, and $C_{1-4}$ alkyl; or two substituents when on the same methylene (CH$_2$) group are taken together with the carbon atom to which they are attached to form a cyclopropyl group;

or $R^2$ and $R^3$ together form a 5- or 6-membered saturated ring fused with a 5- or 6-membered aromatic ring system having 0, 1, or 2 heteroatoms selected from N, O, and S.

These compounds are effective as androgen receptor agonists and are particularly effective as selective androgen receptor agonists (SARMs). They are therefore useful for the treatment of conditions caused by androgen deficiency or which can be ameliorated by androgen administration.

The present invention also relates to pharmaceutical compositions comprising the compounds of the present invention and a pharmaceutically acceptable carrier.

The present invention also relates to methods for the treatment of conditions caused by androgen deficiency or which can be ameliorated by androgen administration in a mammal in need thereof by administering the compounds and pharmaceutical compositions of the present invention.

The present invention also relates to methods for the treatment of osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, arthritic conditions, such as for example, inflammatory arthritis and joint repair, HIV-wasting, prostate cancer, cancer cachexia, muscular dystrophies, premature ovarian failure, and autoimmune disease by administering the compounds and pharmaceutical compositions of the present invention, alone or in combination with a therapeutically effective amount of another agent known to be useful to treat these conditions.

DETAILED DESCRIPTION OF THE INVENTION

The present invention relates to compounds that are useful as androgen receptor agonists, in particular, as selective androgen receptor agonists. Compounds of the present invention are described by structural formula I:

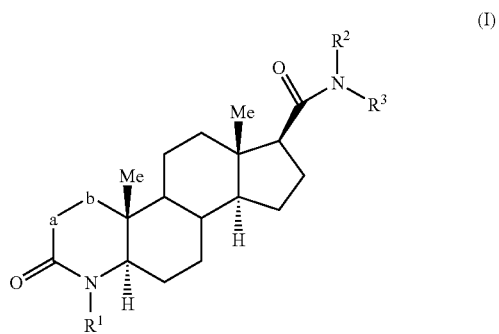

or a pharmaceutically acceptable salt or an enantiomer thereof; wherein
n is 0, 1 or 2;
a–b represents CF=CH, CBFCH$_2$, or CF$_2$CH$_2$;
$R^1$ is hydrogen, hydroxymethyl, or $C_{1-3}$ alkyl, wherein alkyl is unsubstituted or substituted with one to seven fluorine atoms;
$R^2$ is hydrogen or $C_{1-4}$ alkyl;
$R^3$ is selected from
  $C_{1-4}$ alkyl,
  (CH$_2$)$_n$-cycloheteroalkyl, and
  (CH$_2$)$_n$-aryl, wherein aryl is selected from
    (1) phenyl,
    (2) naphthyl,
    (3) benzimidazolyl,
    (4) benzofuranyl,
    (5) benzothiophenyl,
    (6) benzoxazolyl,
    (7) benzothiazolyl,
    (8) benzodihydrofuranyl,
    (9) 1,3-benzodioxolyl,
    (10) 2,3-dihydro-1,4-benzodioxinyl,
    (11) indolyl,
    (12) quinolyl,
    (13) isoquinolyl,
    (14) furanyl,
    (15) thienyl,
    (16) imidazolyl,
    (17) oxazolyl,
    (18) thiazolyl,
    (19) isoxazolyl,
    (20) isothiazolyl,
    (21) pyrazolyl,
    (22) pyrrolyl,
    (23) pyridyl,
    (24) pyrimidyl,

(25) pyrazinyl,
(26) thiadiazolyl,
(27) oxadiazolyl,
(28) triazolyl,
(29) tetrazolyl, and
(30) indanyl;

wherein the alkyl group or the cycloheteroalkyl group is unsubstituted or substituted with one to three substituents independently selected from halogen, hydroxy, and $C_{1-4}$ alkoxy; the aryl group as defined in items (1) to (30) is unsubstituted or substituted with one to three groups independently selected from halogen, phenyl, $C_{1-8}$ alkyl, $C_{3-8}$ cycloalkyl, $C_{3-8}$ cycloheteroalkyl, phenyl-$C_{1-6}$ alkyl, amino-$C_{0-6}$ alkyl, $C_{1-6}$ alkylamino-$C_{0-6}$ alkyl, ($C_{1-6}$ alkyl)$_2$amino-$C_{0-6}$ alkyl, phenyl-$C_{0-6}$ alkylamino-$C_{0-6}$ alkyl, (phenyl-$C_{0-6}$ alkyl)$_2$amino-$C_{0-6}$ alkyl, $C_{1-6}$ alkylthio, phenyl-$C_{0-6}$ alkylthio, $C_{1-6}$ alkylsulfinyl, phenyl-$C_{0-6}$ alkylsulfinyl, $C_{1-6}$ alkylsulfonyl, phenyl-$C_{0-6}$ alkylsulfonyl, $C_{1-6}$ alkoxy-$C_{1-6}$ alkyl, phenyl-$C_{0-6}$ alkoxy-$C_{0-6}$ alkyl, hydroxycarbonyl-$C_{0-6}$ alkyl, $C_{1-6}$ alkoxycarbonyl-$C_{0-6}$ alkyl, phenyl-$C_{0-6}$ alkoxycarbonyl-$C_{0-6}$ alkyl, hydroxycarbonyl-$C_{1-6}$ alkyloxy, hydroxy-$C_{0-6}$ alkyl, cyano, nitro, perfluoro-$C_{1-4}$ alkyl, perfluoro-$C_{1-4}$ alkoxy, oxo, $C_{1-6}$ alkylcarbonyloxy, phenyl-$C_{0-6}$ alkylcarbonyloxy, $C_{1-6}$ alkylcarbonylamino, phenyl-$C_{0-6}$ alkylcarbonylamino, $C_{1-6}$ alkylsulfonylamino, phenyl-$C_{0-6}$ alkylsulfonylamino, $C_{1-6}$ alkoxycarbonylamino, phenyl-$C_{0-6}$ alkoxycarbonylamino, $C_{1-6}$ alkylaminocarbonylamino, phenyl-$C_{0-6}$ alkylaminocarbonylamino, ($C_{1-6}$ alkyl)$_2$ aminocarbonylamino, (phenyl-$C_{0-6}$ alkyl)$_2$ aminocarbonylamino, ($C_{1-6}$ alkyl)$_2$ aminocarbonyloxy, and (phenyl-$C_{0-6}$ alkyl)$_2$ aminocarbonyloxy; and wherein any methylene (CH$_2$) carbon atom in (CH$_2$)$_n$ is unsubstituted or substituted with one to two groups independently selected from halogen, hydroxy, and $C_{1-4}$ alkyl; or two substituents when on the same methylene (CH$_2$) group are taken together with the carbon atom to which they are attached to form a cyclopropyl group;

or $R^2$ and $R^3$ together form a 5- or 6-membered saturated ring fused with a 5- or 6-membered aromatic ring system having 0, 1, or 2 heteroatoms selected from N, O, and S.

In one embodiment of the compounds of the present invention, $R^1$ is hydrogen or methyl. In a class of this embodiment, $R^1$ is methyl.

In a second embodiment of the compounds of the present invention, a-b represents CF=CH.

In a third embodiment of the compounds of the present invention, a-b represents CHFCH$_2$.

In a fourth embodiment of the compounds of the present invention, $R^2$ is hydrogen and $R^3$ is (CH$_2$)$_n$-aryl. In a class of this embodiment, n is 0 or 1.

In a fifth embodiment of the compounds of the present invention, $R^1$ is methyl, a-b represents CF=CH, $R^2$ is hydrogen, and $R^3$ is (CH$_2$)$_n$-aryl. In a class of this embodiment, n is 0 or 1.

In a sixth embodiment of the compounds of the present invention, $R^1$ is methyl, a-b represents CHFCH$_2$, $R^2$ is hydrogen, and $R^3$ is (CH$_2$)$_n$-aryl. In a class of this embodiment, n is 0 or 1.

In another embodiment, $R^1$ is chosen from hydrogen and methyl, a-b is chosen from CHFCH$_2$, $R^2$ is hydrogen, and $R^3$ is (CH$_2$)$_n$-cycloheteroalkyl, In a class of this embodiment, $R^1$ is methyl, and a-b represents CF=CH.

In yet another embodiment of the invention, $R^3$ is chosen from:
$C_{1-4}$ alkyl, and
(CH$_2$)$_n$-aryl, wherein aryl is selected from (1) phenyl,
(2) naphthyl,
(3) benzimidazolyl,
(4) benzofuranyl,
(5) benzothiophenyl,
(6) benzoxazolyl,
(7) benzothiazolyl,
(8) benzodihydrofuranyl,
(9) 1,3-benzodioxolyl,
(10) 2,3-dihydro-1,4-benzodioxinyl,
(11) indolyl,
(12) quinolyl,
(13) isoquinolyl,
(14) furanyl,
(15) thienyl,
(16) imidazolyl,
(17) oxazolyl,
(18) thiazolyl,
(19) isoxazolyl,
(20) isothiazolyl,
(21) pyrazolyl,
(22) pyrrolyl,
(23) pyridyl,
(24) pyrimidyl,
(25) pyrazinyl,
(26) thiadiazolyl,
(27) oxadiazolyl,
(28) triazolyl,
(29) tetrazolyl, and
(30) indanyl;

wherein the alkyl group or the cycloheteroalkyl group is unsubstituted or substituted with one to three substituents independently selected from halogen, hydroxy, and $C_{1-4}$ alkoxy; the aryl group as defined in items (1) to (30) is unsubstituted or substituted with one to three groups independently selected from halogen, phenyl, $C_{1-8}$ alkyl, $C_{3-8}$ cycloalkyl, $C_{3-8}$ cycloheteroalkyl, phenyl-$C_{1-6}$ alkyl, amino-$C_{0-6}$ alkyl, $C_{1-6}$ alkylamino-$C_{0-6}$ alkyl, ($C_{1-6}$ alkyl)$_2$amino-$C_{0-6}$ alkyl, phenyl-$C_{0-6}$ alkylamino-$C_{0-6}$ alkyl, (phenyl-$C_{0-6}$ alkyl)$_2$amino-$C_{0-6}$ alkyl, $C_{1-6}$ alkylthio, phenyl-$C_{0-6}$ alkylthio, $C_{1-6}$ alkylsulfinyl, phenyl-$C_{0-6}$ alkylsulfinyl, $C_{1-6}$ alkylsulfonyl, phenyl-$C_{0-6}$ alkylsulfonyl,
$C_{1-6}$ alkoxy-$C_{0-6}$ alkyl, phenyl-$C_{0-6}$ alkoxy-$C_{0-6}$ alkyl, hydroxycarbonyl-$C_{0-6}$ alkyl, $C_{1-6}$ alkoxycarbonyl-$C_{0-6}$ alkyl, phenyl-$C_{0-6}$ alkoxycarbonyl-$C_{0-6}$ alkyl, hydroxycarbonyl-$C_{1-6}$ alkyloxy, hydroxy-$C_{0-6}$ alkyl, cyano, nitro, perfluoro-$C_{1-4}$ alkyl, perfluoro-$C_{1-4}$ alkoxy, oxo, $C_{1-6}$ alkylcarbonyloxy, phenyl-$C_{0-6}$ alkylcarbonyloxy, $C_{1-6}$ alkylcarbonylamino, phenyl-$C_{0-6}$ alkylcarbonylamino, $C_{1-6}$ alkylsulfonylamino, phenyl-$C_{0-6}$ alkylsulfonylamino, $C_{1-6}$ alkoxycarbonylamino, phenyl-$C_{0-6}$ alkoxycarbonylamino, $C_{1-6}$ alkylaminocarbonylamino, phenyl-$C_{0-6}$ alkylaminocarbonylamino, ($C_{1-6}$ alkyl)$_2$ aminocarbonylamino, (phenyl-$C_{0-6}$ alkyl)$_2$ aminocarbonylamino, ($C_{1-6}$ alkyl)$_2$ aminocarbonyloxy, and (phenyl-$C_{0-6}$ alkyl)$_2$ aminocarbonyloxy; and wherein any methylene (CH$_2$) carbon atom in (CH$_2$)$_n$ is unsubstituted or substituted with one to two groups independently selected from halogen, hydroxy, and $C_{1-4}$ alkyl; or two substituents when on the same methylene (CH$_2$) group are taken together with the carbon atom to which they are attached to form a cyclopropyl group.

Illustrative but nonlimiting examples of compounds of the present invention that are useful as androgen receptor modulators are the following:

N-(2,2,2-trifluoroethyl)-2-fluoro-4-methyl-3-oxo-4-aza-5α-androst-1-en-17β-carboxamide;
N-(2-fluorophenylmethyl)-2-fluoro-4-methyl-3-oxo-4-aza-5α-androst-1-en-17β-carboxamide;
N-(3-fluorophenylmethyl)-2-fluoro-4-methyl-3-oxo-4-aza-5α-androst-1-en-17β-carboxamide;
N-(2-trifluoromethylphenyl)-2-fluoro-4-methyl-3-oxo-4-aza-5α-androst-1-en-17β-carboxamide;
N-(2-chlorophenyl)-2-fluoro-4-methyl-3-oxo-4-aza-5α-androst-1-en-17β-carboxamide;
N-(4-methoxyphenyl)-2-fluoro-4-methyl-3-oxo-4-aza-5α-androst-1-en-17β-carboxamide;
N-(3-methoxyphenyl)-2-fluoro-4-methyl-3-oxo-4-aza-5α-androst-1-en-17β-carboxamide;
N-(2-methylphenyl)-2-fluoro-4-methyl-3-oxo-4-aza-5α-androst-1-en-17β-carboxamide;
N-(3-methylphenyl)-2-fluoro-4-methyl-3-oxo-4-aza-5α-androst-1-en-17β-carboxamide;
N-(2-fluorophenyl)-2-fluoro-4-methyl-3-oxo-4-aza-5α-androst-1-en-17β-carboxamide;
N-(3-fluorophenyl)-2-fluoro-4-methyl-3-oxo-4-aza-5α-androst-1-en-17β-carboxamide;
N-(4-fluorophenyl)-2-fluoro-4-methyl-3-oxo-4-aza-5α-androst-1-en-17β-carboxamide;
N-(4-chloro-2-fluorophenyl)-2-fluoro-4-methyl-3-oxo-4-aza-5α-androst-1-en-17β-carboxamide;
N-(2,4-difluorophenyl)-2-fluoro-4-methyl-3-oxo-4-aza-5α-androst-1-en-17β-carboxamide;
N-(α-methylphenylmethyl)-2-fluoro-4-methyl-3-oxo-4-aza-5α-androst-1-en-17β-carboxamide;
N-(phenyl)-2-fluoro-4-methyl-3-oxo-4-aza-5α-androst-1-en-17β-carboxamide;
N-(4-chloro-2-trifluoromethylphenyl)-2-fluoro-4-methyl-3-oxo-4-aza-5α-androst-1-en-17β-carboxamide;
N-(5-methylpyridin-2-yl)-2-fluoro-4-methyl-3-oxo-4-aza-5α-androst-1-en-17β-carboxamide;
N-(thiophen-2-ylmethyl)-2-fluoro-4-methyl-3-oxo-4-aza-5α-androst-1-en-17β-carboxamide;
N-(thiophen-3-ylmethyl)-2-fluoro-4-methyl-3-oxo-4-aza-5α-androst-1-en-17β-carboxamide;
N-(2-trifluoromethylphenylmethyl)-2-fluoro-4-methyl-3-oxo-4-aza-5α-androst-1-en-17β-carboxamide;
N-(benzimidazol-2-ylmethyl)-2-fluoro-4-methyl-3-oxo-4-aza-5α-androst-1-en-17β-carboxamide;
N-(1-methylbenzimidazol-2-ylmethyl)-2-fluoro-4-methyl-3-oxo-4-aza-5α-androst-1-en-17β-carboxamide;
N-(1-methyl-5-trifluoromethylbenzimidazol-2-ylmethyl)-2-fluoro-4-methyl-3-oxo-4-aza-5α-androst-1-en-17β-carboxamide;
N-(5-chlorobenzimidazol-2-ylmethyl)-2-fluoro-4-methyl-3-oxo-4-aza-5α-androst-1-en-17β-carboxamide;
N-(5-methoxybenzimidazol-2-ylmethyl)-2-fluoro-4-methyl-3-oxo-4-aza-5α-androst-1-en-17β-carboxamide;
N-(benzthiazol-2-ylmethyl)-2-fluoro-4-methyl-3-oxo-4-aza-5α-androst-1-en-17β-carboxamide;
N-(2,3-dihydro-1,4-benzodioxin-2-ylmethyl)-2-fluoro-4-methyl-3-oxo-4-aza-5α-androst-1-en-17β-carboxamide;
N-(thiazol-2-ylmethyl)-2-fluoro-4-methyl-3-oxo-4-aza-5α-androst-1-en-17β-carboxamide;
N-(4-methylthiazol-2-ylmethyl)-2-fluoro-4-methyl-3-oxo-4-aza-5α-androst-1-en-17β-carboxamide;
N-(thiazol-4-ylmethyl)-2-fluoro-4-methyl-3-oxo-4-aza-5α-androst-1-en-17β-carboxamide;
N-(1-methylimidazol-2-ylmethyl)-2-fluoro-4-methyl-3-oxo-4-aza-5α-androst-1-en-17β-carboxamide;
N-(tetrahydro-2H-pyran-2(S)-ylmethyl)-2-fluoro-4-methyl-3-oxo-4-aza-5α-androst-1-en-17β-carboxamide;
N-(tetrahydro-2H-pyran-2(R)-ylmethyl)-2-fluoro-4-methyl-3-oxo-4-aza-5α-androst-1-en-17β-carboxamide;
N-(2,3-dihydro-1,4-benzodioxin-2(R)-ylmethyl)-2-fluoro-4-methyl-3-oxo-4-aza-5α-androst-1-en-17β-carboxamide;
N-(2,3-dihydro-1,4-benzodioxin-2(S)-ylmethyl)-2-fluoro-4-methyl-3-oxo-4-aza-5α-androst-1-en-17β-carboxamide;
N-(tetrahydrofuran-2(S)-ylmethyl)-2-fluoro-4-methyl-3-oxo-4-aza-5α-androst-1-en-17β-carboxamide;
N-(tetrahydrofuran-2(R)-ylmethyl)-2-fluoro-4-methyl-3-oxo-4-aza-5α-androst-1-en-17β-carboxamide;
N-(3H-imidazo[4,5-b]pyridin-2-ylmethyl)-2-fluoro-4-methyl-3-oxo-4-aza-5α-androst-1-en-17β-carboxamide;
N-(2-fluorophenylmethyl)-2α-fluoro-4-methyl-3-oxo-4-aza-5α-androstan-17β-carboxamide;
N-(2-trifluoromethylphenylmethyl)-2α-fluoro-4-methyl-3-oxo-4-aza-5α-androstan-17β-carboxamide;
N-(3-methoxyphenyl)-2α-fluoro-4-methyl-3-oxo-4-aza-5α-androstan-17β-carboxamide;
N-(4-methoxyphenyl)-2α-fluoro-4-methyl-3-oxo-4-aza-5α-androstan-17β-carboxamide;
N-(2-trifluoromethylphenyl)-2α-fluoro-4-methyl-3-oxo-4-aza-5α-androstan-17β-carboxamide;
N-(2-chlorophenyl)-2α-fluoro-4-methyl-3-oxo-4-aza-5α-androstan-17β-carboxamide;
N-(2-fluorophenylmethyl)-2α-fluoro-4-methyl-3-oxo-4-aza-5α-androstan-17β-carboxamide;
N-(benzimidazol-2-ylmethyl)-2α-fluoro-4-methyl-3-oxo-4-aza-5α-androstan-17β-carboxamide;
N-(1-methylbenzimidazol-2-ylmethyl)-2α-fluoro-4-methyl-3-oxo-4-aza-5α-androstan-17β-carboxamide;
N-(thiazol-2-ylmethyl)-2α-fluoro-4-methyl-3-oxo-4-aza-5α-androstan-17β-carboxamide;
N-(furan-2-ylmethyl)-2α-fluoro-4-methyl-3-oxo-4-aza-5α-androstan-17β-carboxamide; and
N-(thiophen-2-ylmethyl)-2α-fluoro-4-methyl-3-oxo-4-aza-5α-androstan-17β-carboxamide;

pharmaceutically acceptable salts and enantiomers thereof.

In yet another embodiment of the invention, the compounds of the present invention are chosen from:
N-(2-fluorophenylmethyl)-2-fluoro-4-methyl-3-oxo-4-aza-5α-androst-1-en-17β-carboxamide;
N-(3-fluorophenylmethyl)-2-fluoro-4-methyl-3-oxo-4-aza-5α-androst-1-en-17β-carboxamide;
N-(5-chlorobenzimidazol-2-ylmethyl)-2-fluoro-4-methyl-3-oxo-4-aza-5α-androst-1-en-17β-carboxamide;
N-(5-methoxybenzimidazol-2-ylmethyl)-2-fluoro-4-methyl-3-oxo-4-aza-5α-androst-1-en-17β-carboxamide;
N-(benzthiazol-2-ylmethyl)-2-fluoro-4-methyl-3-oxo-4-aza-5α-androst-1-en-17β-carboxamide;
N-(tetrahydro-2H-pyran-2(S)-ylmethyl)-2-fluoro-4-methyl-3-oxo-4-aza-5α-androst-1-en-17β-carboxamide;
N-(tetrahydro-2H-pyran-2(R)-ylmethyl)-2-fluoro-4-methyl-3-oxo-4-aza-5α-androst-1-en-17β-carboxamide;
N-(2,3-dihydro-1,4-benzodioxin-2(R)-ylmethyl)-2-fluoro-4-methyl-3-oxo-4-aza-5α-androst-1-en-17β-carboxamide;
N-(2,3-dihydro-1,4-benzodioxin-2(S)-ylmethyl)-2-fluoro-4-methyl-3-oxo-4-aza-5α-androst-1-en-17β-carboxamide;
N-(tetrahydrofuran-2(S)-ylmethyl)-2-fluoro-4-methyl-3-oxo-4-aza-5α-androst-1-en-17β-carboxamide;
N-(tetrahydrofuran-2(R)-ylmethyl)-2-fluoro-4-methyl-3-oxo-4-aza-5α-androst-1-en-17β-carboxamide;
N-(3H-imidazo[4,5-b]pyridin-2-ylmethyl)-2-fluoro-4-methyl-3-oxo-4-aza-5α-androst-1-en-17β-carboxamide;

N-(2-fluorophenylmethyl)-2α-fluoro-4-methyl-3-oxo-4-aza-5α-androstan-17β-carboxamide;
N-(thiazol-2-ylmethyl)-2α-fluoro-4-methyl-3-oxo-4-aza-5α-androstan-17β-carboxamide;
N-(furan-2-ylmethyl)-2α-fluoro-4-methyl-3-oxo-4-aza-5α-androstan-17β-carboxamide; and
N-(thiophen-2-ylmethyl)-2α-fluoro-4-methyl-3-oxo-4-aza-5α-androstan-17β-carboxamide;

pharmaceutically acceptable salts and enantiomers thereof.

In yet another variant, the compounds of the present invention are chosen from:
N-(tetrahydro-2H-pyran-2(S)-ylmethyl)-2-fluoro-4-methyl-3-oxo-4-aza-5α-androst-1-en-17β-carboxamide;
N-(tetrahydro-2H-pyran-2(R)-ylmethyl)-2-fluoro-4-methyl-3-oxo-4-aza-5α-androst-1-en-17β-carboxamide;
N-(2,3-dihydro-1,4-benzodioxin-2(R)-ylmethyl)-2-fluoro-4-methyl-3-oxo-4-aza-5α-androst-1-en-17β-carboxamide;
N-(2,3-dihydro-1,4-benzodioxin-2(S)-ylmethyl)-2-fluoro-4-methyl-3-oxo-4-aza-5α-androst-1-en-17β-carboxamide;
N-(tetrahydrofuran-2(S)-ylmethyl)-2-fluoro-4-methyl-3-oxo-4-aza-5α-androst-1-en-17β-carboxamide;
N-(tetrahydrofuran-2(R)-ylmethyl)-2-fluoro-4-methyl-3-oxo-4-aza-5α-androst-1-en-17β-carboxamide;
N-(3H-imidazo[4,5-b]pyridin-2-ylmethyl)-2-fluoro-4-methyl-3-oxo-4-aza-5α-androst-1-en-17β-carboxamide;

pharmaceutically acceptable salts and enantiomers thereof.

In one embodiment of the invention, the compounds are chosen from:
N-(2-fluorophenylmethyl)-2-fluoro-4-methyl-3-oxo-4-aza-5α-androst-1-en-17β-carboxamide;
N-(3-fluorophenylmethyl)-2-fluoro-4-methyl-3-oxo-4-aza-5α-androst-1-en-17β-carboxamide;
N-(5-chlorobenzimidazol-2-ylmethyl)-2-fluoro-4-methyl-3-oxo-4-aza-5α-androst-1-en-17β-carboxamide;
N-(5-methoxybenzimidazol-2-ylmethyl)-2-fluoro-4-methyl-3-oxo-4-aza-5α-androst-1-en-17β-carboxamide;
N-(benzthiazol-2-ylmethyl)-2-fluoro-4-methyl-3-oxo-4-aza-5α-androst-1-en-17β-carboxamide;
N-(2-fluorophenylmethyl)-2α-fluoro-4-methyl-3-oxo-4-aza-5α-androstan-17β-carboxamide;
N-(thiazol-2-ylmethyl)-2α-fluoro-4-methyl-3-oxo-4-aza-5α-androstan-17β-carboxamide;
N-(furan-2-ylmethyl)-2α-fluoro-4-methyl-3-oxo-4-aza-5α-androstan-17β-carboxamide; and
N-(thiophen-2-ylmethyl)-2α-fluoro-4-methyl-3-oxo-4-aza-5α-androstan-17β-carboxamide;

pharmaceutically acceptable salts and enantiomers thereof.

The compounds of the present invention can have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein can exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof. Here, X represents the remainder of the fluorinated 4-azasteroid derivatives of the present invention.

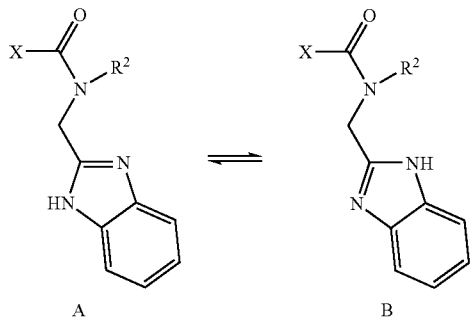

A                           B

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.). The term "$C_0$ alkyl" (as in "$C_{0-8}$ alkylaryl") shall refer to the absence of an alkyl group.

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "alkylidene" shall mean a straight or branched chain alkylidene group of one to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "cycloheteroalkyl," as used herein, shall mean a 3- to 8-membered fully saturated heterocyclic ring containing one or two heteroatoms chosen from N, O, or S. Examples of cycloheteroalkyl groups include, but are not limited to, piperidinyl, pyrrolidinyl, azetidinyl, morpholinyl, oxacyclopentane, oxacyclohexane, and piperazinyl. In one embodiment of the present invention, cycloheteroalkyl is selected from piperidinyl, pyrrolidinyl, oxacyclopentane, oxacyclohexane, and morpholinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or bicyclic system comprising at least one aromatic ring, wherein the monocylic or bicyclic system contains 0, 1, 2, 3, or 4 heteroatoms chosen from N, O, or S, and wherein the monocylic or bicylic system is either unsubstituted or substituted with one or more groups independently selected from halogen, phenyl, $C_{1-8}$ alkyl, $C_{3-8}$ cycloalkyl, $C_{3-8}$ cycloheteroalkyl, phenyl-$C_{1-6}$ alkyl, amino-$C_{0-6}$ alkyl, $C_{1-6}$ alkylamino-$C_{0-6}$ alkyl, ($C_{1-6}$ alkyl)$_2$amino-$C_{0-6}$alkyl, phenyl-$C_{0-6}$ alkylamino-$C_{0-6}$alkyl, (phenyl-$C_{0-6}$ alkyl)$_2$amino-$C_{0-6}$ alkyl, $C_{1-6}$ alkylthio, phenyl-$C_{0-6}$ alkylthio, $C_{1-6}$ alkylsulfinyl, phenyl-$C_{0-6}$ alkylsulfinyl, $C_{1-6}$ alkylsulfonyl, phenyl-$C_{0-6}$ alkylsulfonyl, $C_{1-6}$ alkoxy-$C_{0-6}$alkyl, phenyl-$C_{0-6}$ alkoxy-$C_{0-6}$ alkyl, hydroxycarbonyl-$C_{0-6}$ alkyl, $C_{1-6}$ alkoxycarbonyl-$C_{0-6}$ alkyl, phenyl-$C_{0-6}$ alkoxycarbonyl-$C_{0-6}$alkyl, hydroxycarbonyl $C_{1-6}$ alkyloxy, hydroxy-$C_{0-6}$ alkyl, cyano, nitro, perfluoro$C_{1-4}$ alkyl, perfluoro$C_{1-4}$ alkoxy, oxo, $C_{1-6}$ alkylcarbonyloxy, phenyl-$C_{0-6}$ alkylcarbonyloxy, $C_{1-6}$ alkylcarbonylamino, phenyl-$C_{0-6}$ alkylcarbonylamino, $C_{1-6}$ alkylsulfonylamino, phenyl-$C_{0-6}$ alkylsulfonylamino, $C_{1-6}$ alkoxycarbonylamino, phenyl-$C_{0-6}$ alkoxycarbonylamino, $C_{1-6}$ alkylaminocarbonylamino, phenyl-$C_{0-6}$ alkylaminocarbonylamino, $(C_{1-6}$ alkyl$)_2$ aminocarbonylamino, (phenyl-$C_{0-6}$ alkyl$)_2$ aminocarbonylamino, $(C_{1-6}$ alkyl$)_2$ aminocarbonyloxy, and (phenyl-$C_{0-6}$ alkyl$)_2$ aminocarbonyloxy. Preferably, the aryl group is unsubstituted, mono-, di-, or tri-substituted with one to three of the above-named substituents; more preferably, the aryl group is unsubstituted, mono- or di-substituted with one to two of the above-named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{0-8}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When any variable (e.g., $R^2$, $R^3$, etc.) occurs more than one time in any substituent or in formula I, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

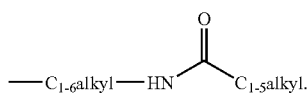

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Compounds of the present invention have been found to be tissue-selective modulators of the androgen receptor (SARMs). In one aspect, compounds of the present invention may be useful to activate the function of the androgen receptor in a mammal, and in particular to activate the function of the androgen receptor in bone and/or muscle tissue and block or inhibit ("antagonize") the function of the androgen receptor in the prostate of a male individual or in the uterus of a female individual. The activation of the AR in bone can be assayed through stimulation of bone formation in a rodent model of osteoporosis, and the antagonism of the AR in the prostate can be assayed through observation of minimal effects on prostate growth in castrated rodents and antagonism of prostate growth induced by AR agonists, as detailed in the Examples.

A further aspect of the present invention is concerned with compounds of structural formula I that block the function of the androgen receptor in the prostate of a male individual or in the uterus of a female individual induced by AR agonists, but not in hair-growing skin or vocal cords, and activate the function of the androgen receptor in bone and/or muscle tissue, but not in organs which control blood lipid levels (e.g. liver).

The compounds of the present invention may be used to treat conditions which are caused by androgen deficiency or which can be ameliorated by androgen replacement, including, but not limited to osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, arthritic conditions, such as for example, inflammatory arthritis and joint repair, HIV-wasting, prostate cancer, cancer cachexia, muscular dystrophies, premature ovarian failure, and autoimmune disease, alone or in combination with other active agents. Treatment is effected by administration of a therapeutically effective amount of a compound of structural formula I to a mammal in need of such treatment. In addition, these compounds are useful as ingredients in pharmaceutical compositions alone or in combination with other active agents.

In one embodiment, the compounds of the present invention may be used to treat conditions in a male individual which are caused by androgen deficiency or which can be ameliorated by androgen replacement, including, but not limited to, osteoporosis, osteopenia, glucocorticoid-induced osteoporosis, periodontal disease, HIV-wasting, prostate cancer, cancer cachexia, obesity, aplastic and other anemias, and muscular dystrophies, alone or in combination with other active agents. Treatment is effected by administration of a therapeutically effective amount of a compound of structural formula I to a male individual in need of such treatment.

"Arthritic condition" or "arthritic conditions" refers to a disease wherein inflammatory lesions are confined to the joints or any inflammatory conditions of the joints, most notably osteoarthritis and rheumatoid arthritis (Academic Press Dictionary of Science Technology; Academic Press; 1st edition, Jan. 15, 1992). The compounds of Formula I are also useful, alone or in combination, to treat or prevent arthritic conditions, such as Behcet's disease; bursitis and tendinitis; CPPD deposition disease; carpal tunnel syndrome; Ehlers-Danlos syndrome; fibromyalgia; gout; infectious arthritis; inflammatory bowel disease; juvenile arthritis; lupus erythematosus; lyme disease; marfan syndrome; myositis; osteoarthritis; osteogenesis imperfecta; osteonecrosis; polyarteritis; polymyalgia rheumatica; psoriatic arthritis; Raynaud's phenomenon; reflex sympathetic dystrophy syndrome; Reiter's syndrome; rheumatoid arthritis; scleroderma; and Sjogren's syndrome. An embodiment of the invention encompasses the treatment or prevention of an arthrtic condition which comprises administering a therapeutically effective amount of a Compound of Formula I. A subembodiment is the treatment or prevention of osteoarthritis which comprises administering a therapeutically effective amount of a Compound of Formula I. See: Cutolo M, Seriolo B, Villaggio B, Pizzorni C, Craviotto C, Sulli A. *Ann. N.Y. Acad. Sci.* 2002 Jun;966:131–42; Cutolo, *M. Rheum Dis Clin North Am* 2000 Nov;26(4):881–95; Bijlsma J W, Van den Brink H R. Am J Reprod Immunol 1992 October–December;28(3–4):231–4; Jansson L, Holmdahl R.; *Arthritis Rheum* 2001 September;44(9):2168–75; and Purdie D W. Br *Med Bull* 2000;56(3):809–23. Also, see Merck Manual, 17th edition, pp. 449–451.

When used in combination to treat arthritic conditions, the Compounds of Formula I can be used with any of the drugs diclosed herein as useful for combination therapy, or can be used with drugs known to treat or prevent arrthritic conditions, such as corticosteroids, cytoxic drugs (or other disease modifying or remission inducing drugs), gold treatment, methotrexate, NSAIDs, and COX-2 inhibitors.

In another embodiment, the compounds of the present invention may be used to treat conditions in a female individual which are caused by androgen deficiency or which can be ameliorated by androgen replacement, including, but not limited to, osteoporosis, osteopenia, glucocorticoid-induced osteoporosis, postmenopausal symptoms, periodontal disease, HIV-wasting, cancer cachexia, obesity, aplastic and other anemias, muscular dystrophies, premature ovarian failure, and autoimmune disease, alone or in combination with other active agents. Treatment is effected by administration of a therapeutically effective amount of a compound of structural formula I to a female individual in need of such treatment.

The compounds of structural formula I may also be employed as adjuncts to traditional androgen depletion therapy in the treatment of prostate cancer to restore bone, minimize bone loss, and maintain or increase bone mineral density. In this manner, they may be employed together with traditional androgen deprivation therapy, including GnRH agonists/antagonists, such as those disclosed in P. Limonta, et al., "LHRH analogues as anticancer agents: pituitary and extrapituitary sites of action," *Exp. Opin. Invest. Drugs,* 10: 709–720 (2001); H. J. Stricker, "Luteinizing hormone-releasing hormone antagonists," *Urology,* 58 (Suppl. 2A): 24–27 (2001); R. P. Millar, et al., "Progress towards the development of non-peptide orally-active GnRH antagonists," *British Medical Bulletin,* 56: 761–772 (2000); and A. V. Schally et al., "Rational use of agonists and antagonists of LH-RH in the treatment of hormone-sensitive neoplasms and gynecologic conditions," *Advanced Drug Delivery Reviews,* 28: 157–169 (1997). It is also possible that the compounds of structural formula I may be used in combination with antiandrogens, such as flutamide, 2-hydroxyflutamide (the active metabolite of flutamide), nilutamide, and bicalutamide (Casodex™) in the treatment of prostate cancer.

Further, the compounds of the present invention may also be employed in the treatment of pancreatic cancer, either for their androgen antagonist properties or as an adjunct to an antiandrogen, such as flutamide, 2-hydroxyflutamide (the active metabolite of flutamide), nilutamide, and bicalutamide (Casodex™).

Compounds of structural formula I have minimal negative effects on lipid metabolism. Therefore, considering their tissue selective androgen agonistic properties, the compounds of this invention have advantages over existing approaches for hormone replacement therapy in hypogonadic (androgen deficient) male individuals.

Additionally, compounds of the present invention can increase the number of blood cells, such as red blood cells and platelets, and can be used for treatment of hematopoietic disorders, such as aplastic anemia.

Representative compounds of the present invention typically display submicromolar binding affinity for the androgen receptor. Compounds of this invention are therefore useful in treating mammals suffering from disorders related to androgen receptor function. Pharmacologically effective amounts of the compound, including the pharmaceutically effective salts thereof, are administered to the mammal, to treat disorders related to androgen receptor function, or which can be improved by the addition of additional androgen, such as osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, arthritic conditions, for example, inflammatory arthritis, and joint repair.

It is generally preferable to administer compounds of the present invention in their enantiomerically pure form. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

As used herein, a compound of the present invention which functions as an "agonist" of the androgen receptor can bind to the androgen receptor and initiate a physiological or a pharmacological response characteristic of that receptor. The term "tissue-selective androgen receptor modulator" refers to an androgen receptor ligand that mimics the action of a natural ligand in some tissues but not in others. A "partial agonist" is an agonist which is unable to induce maximal activation of the receptor population, regardless of the amount of compound applied. A "full agonist" induces full activation of the androgen receptor population at a given concentration. A compound of the present invention which functions as an "antagonist" of the androgen receptor can bind to the androgen receptor and block or inhibit the androgen-associated responses normally induced by a natural androgen receptor ligand.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant that the carrier, diluent or excipient must be compatible with the other ingredients of the formulation and not be deleterious to the recipient thereof.

The terms "administration of a compound" and "administering a compound" should be understood to mean providing a compound of the invention or a prodrug of a compound of the invention to the individual in need of treatment.

By the term "modulating a function mediated by the androgen receptor in a tissue selective manner" is meant modulating a function mediated by the androgen receptor selectively (or discriminately) in anabolic (bone and/or muscular) tissue (bone and muscular) in the absence of such modulation at androgenic (reproductive) tissue, such as the prostate, testis, seminal vesicles, ovary, uterus, and other sex accessory tissues. In one embodiment the function of the androgen receptor in anabolic tissue is activated whereas the function of the androgen receptor in androgenic tissue is blocked or suppressed.

The administration of a compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

Generally, the daily dosage of a compound of structural formula I may be varied over a wide range from 0.01 to 1000 mg per adult human per day. Most preferably, dosages range from 0.1 to 200 mg/day. For oral administration, the compositions are preferably provided in the form of tablets containing 0.01 to 1000 mg, particularly 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the mammal to be treated.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through an intravenous solution, the dosage administration will, of course, be continuous rather than intermittent throughout the dosage regimen.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Formulations of the tissue-selective androgen receptor modulator employed in the present method for medical use comprise a compound of structural formula I together with an acceptable carrier thereof and optionally other therapeutically active ingredients. The carrier must be pharmaceutically acceptable in the sense of being compatible with the other ingredients of the formulation and not being deleterious to the recipient subject of the formulation.

The present invention, therefore, further provides a pharmaceutical formulation comprising a compound of structural formula I together with a pharmaceutically acceptable carrier thereof.

The formulations include those suitable for oral, rectal, intravaginal, topical or parenteral (including subcutaneous, intramuscular and intravenous administration). Preferred formulations are those suitable for oral administration.

The formulations may be presented in a unit dosage form and may be prepared by any of the methods known in the art of pharmacy. All methods include the step of bringing the active compound in association with a carrier which constitutes one or more ingredients. In general, the formulations are prepared by uniformly and intimately bringing the active compound in association with a liquid carrier, a waxy solid carrier or a finely divided solid carrier, and then, if needed, shaping the product into the desired dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet may be made by compression or molding, optionally with one or more accessory ingredients. Compressed tablets may be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like, may be made by adding the active compound to the solution or suspension. Additional dispersing agents which may be employed include glycerin and the like.

Formulations for vaginal or rectal administration may be presented as a suppository with a conventional carrier, i.e., a base that is nontoxic and nonirritating to mucous membranes, compatible with a compound of structural formula I, and is stable in storage and does not bind or interfere with the release of the compound of structural formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethylene-oxide polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations that comprise a sterile aqueous preparation of the active compound which is preferably isotonic with the blood of the recipient. Such formulations suitably comprise a solution or suspension of a compound that is isotonic with the blood of the recipient subject. Such formulations may contain distilled water, 5% dextrose in distilled water or saline and the active compound. Often it is useful to employ a pharmaceutically and pharmacologically acceptable acid addition salt of the active compound that has appropriate solubility for the solvents employed. Useful formulations also comprise concentrated solutions or solids comprising the active compound which on dilution with an appropriate solvent give a solution suitable for parenteral administration.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

The pharmaceutical composition and method of the present invention may further comprise other therapeutically active compounds usually applied in the treatment of the above mentioned conditions, including osteoporosis, periodontal disease, bone fracture, bone damage following bone reconstructive surgery, sarcopenia, frailty, aging skin, male hypogonadism, post-menopausal symptoms in women, atherosclerosis, hypercholesterolemia, hyperlipidemia, aplastic anemia and other hematopoietic disorders, pancreatic cancer, arthritic conditions, such as inflammatory arthritis, and joint repair.

For the treatment and prevention of osteoporosis, the compounds of the present invention may be administered in combination with a bone-strengthening agent selected from antiresorptive agents, osteoanabolic agents, and other agents beneficial for the skeleton through mechanisms which are not precisely defined, such as calcium supplements, flavonoids, and vitamin D analogs. The conditions of periodontal disease, bone fracture, and bone damage following bone reconstructive surgery may also benefit from these combined treatments. For example, the compounds of the instant invention may be effectively administered in combination with effective amounts of other agents such as estrogens, bisphosphonates, SERMs, cathepsin K inhibitors, $\alpha v \beta 3$ integrin receptor antagonists, vacuolar ATPase inhibitors, the polypeptide osteoprotegerin, antagonists of VEGF, thiazolidinediones, calcitonin, protein kinase inhibitors, parathyroid hormone (PTH) and analogs, calcium receptor antagonists, growth hormone secretagogues, growth hormone releasing hormone, insulin-like growth factor, bone morphogenetic protein (BMP), inhibitors of BMP antagonism, prostaglandin derivatives, fibroblast growth factors, vitamin D and derivatives thereof, vitamin K and derivatives thereof, soy isoflavones, calcium salts, and fluoride salts. The conditions of periodontal disease, bone fracture, and bone damage following bone reconstructive surgery may also benefit from these combined treatments. In one embodiment of the present invention, a compound of the instant invention may be effectively administered in combination with an effective amount of a bone-strengthening agent selected from estrogen or an estrogen derivative, alone or in combination with a progestin or progestin derivative; a bisphosphonate; an antiestrogen or a selective estrogen receptor modulator; an $\alpha v \beta 3$ integrin receptor antagonist; a cathepsin K inhibitor; an osteoclast vacuolar ATPase inhibitor; calcitonin; and osteoprotegerin.

In the treatment of osteoporosis, the activity of the compounds of the present invention are distinct from that of the anti-resorptive agents: estrogens, bisphosphonates, SERMs, calcitonin, cathepsin K inhibitors, vacuolar ATPase inhibitors, agents interfering with the RANK/RANKL/Osteoprotegerin pathway, p38 inhibitors or any other inhibitors of osteoclast generation or osteoclast activation. Rather than inhibiting bone resorption, the compounds of structural formula I stimulate bone formation, acting preferentially on cortical bone, which is responsible for a significant part of bone strength. The thickening of cortical bone substantially contributes to a reduction in fracture risk, especially fractures of the hip. The combination of the tissue-selective androgen receptor modulators of structural formula I with anti-resorptive agents such as estrogen, bisphosphonates, antiestrogens, SERMs, calcitonin, (αvβ3 integrin receptor antagonists, HMG-CoA reductase inhibitors, vacuolar ATPase inhibitors, and cathepsin K inhibitors is particularly useful because of the complementarity of the bone anabolic and antiresorptive actions.

Bone antiresorptive agents are those agents which are known in the art to inhibit the resorption of bone and include, for example, estrogen and estrogen derivatives which include steroidal compounds having estrogenic activity such as, for example, 17β-estradiol, estrone, conjugated estrogen (PREMARIN®), equine estrogen, 17β-ethynyl estradiol, and the like. The estrogen or estrogen derivative may be employed alone or in combination with a progestin or progestin derivative. Nonlimiting examples of progestin derivatives are norethindrone and medroxy-progesterone acetate.

Bisphosphonates are also bone anti-resorptive agents. Bisphosphonate compounds which may also be employed in combination with a compound of structural formula I of the present invention include:

(a) alendronic acid: (4-amino-1-hydroxybutylidene)-bis-phosphonic acid;
(b) alendronate (also known as alendronate sodium or monosodium trihydrate): (4-amino-1-hydroxybutylidene)-bis-phosphonate monosodium trihydrate (alendronic acid and alendronate are described in U.S. Pat. No. 4,922,007, to Kieczykowski et al., issued May 1, 1990, and U.S. Pat. No. 5,019,651, to Kieczykowski, issued May 28, 1991, both of which are incorporated by reference herein in their entirety);
(c) [(cycloheptylamino)-methylene]-bis-phosphonate (incadronate), which is described in U.S. Pat. No. 4,970,335, to Isomura et al., issued Nov. 13, 1990, which is incorporated by reference herein in its entirety;
(d) (dichloromethylene)-bis-phosphonic acid (clodronic acid) and the disodium salt (clodronate), which are described in Belgium Patent 672,205 (1966) and *J. Org. Chem* 32, 4111 (1967), both of which are incorporated by reference herein in their entirety;
(e) [1-hydroxy-3-(1-pyrrolidinyl)-propylidene]-bis-phosphonate (EB-1053);
(f) (1-hydroxyethylidene)-bis-phosphonate (etidronate);
(g) [1-hydroxy-3-(methylpentylamino)propylidene]-bis-phosphonate (ibandronate), which is described in U.S. Pat. No. 4,927,814, issued May 22, 1990, which is incorporated by reference herein in its entirety;
(h) (6-amino-1-hydroxyhexylidene)-bis-phosphonate (neridronate);
(i) [3-(dimethylamino)-1-hydroxypropylidene]-bis-phosphonate (olpadronate);
(j) (3-amino-1-hydroxypropylidene)-bis-phosphonate (pamidronate);
(k) [2-(2-pyridinyl)ethylidene]-bis-phosphonate (piridronate), which is described in U.S. Pat. No. 4,761,406, which is incorporated by reference herein in its entirety;
(l) [1-hydroxy-2-(3-pyridinyl)-ethylidene]-bis-phosphonate (risedronate);
(m) {[(4-chlorophenyl)thio]methylene}-bis-phosphonate (tiludronate), which is described in U.S. Pat. No. 4,876,248, to Breliere et al., Oct. 24, 1989, which is incorporated by reference herein in its entirety;
(n) [1-hydroxy-2-(1H-imidazol-1-yl)ethylidene]-bis-phosphonate (zoledronate); and
(o) [1-hydroxy-2-imidazopyridin-(1,2-a)-3-ylethylidene]-bis-phosphonate (minodronate).

In one embodiment of the methods and compositions of the present invention, the bisphosphonate is selected from alendronate, clodronate, etidronate, ibandronate, incadronate, minodronate, neridronate, olpadronate, pamidronate, piridronate, risedronate, tiludronate, and zoledronate, and pharmaceutically acceptable salts thereof, and mixtures thereof. In a class of this embodiment, the bisphosphonate is selected from alendronate, risedronate, zoledronate, ibandronate, tiludronate, and clodronate. In a subclass of this class, the bisphosphonate is alendronate, pharmaceutically acceptable salts and hydrates thereof, and mixtures thereof. A particular pharmaceutically acceptable salt of alendronate is alendronate monosodium. Pharmaceutically acceptable hydrates of alendronate monosodium include the monohydrate and the trihydrate. A particular pharmaceutically acceptable salt of risedronate is risedronate monosodium. Pharmaceutically acceptable hydrates of risedronate monosodium include the hemi-pentahydrate.

As used throughout this specification and claims, the term "alendronic acid" includes the related bisphosphonic acid forms, pharmaceutically acceptable salt forms, and equilibrium mixtures of these. It includes crystalline, hydrated crystalline, and amorphous forms of alendronic acid and pharmaceutically acceptable salts thereof. It specifically includes anhydrous alendronate monosodium, alendronate monosodium monohydrate, and alendronate monosodium trihydrate.

Still further, antiestrogenic compounds such as raloxifene (see, e.g., U.S. Pat. No. 5,393,763), clomiphene, zuclomiphene, enclomiphene, nafoxidene, CI-680, CI-628, CN-55,945-27, Mer-25, U-11,555A, U-100A, and salts thereof, and the like (see, e.g., U.S. Pat. Nos. 4,729,999 and 4,894,373) may be employed in combination with a compound of structural formula I in the methods and compositions of the present invention. These agents are also known as SERMs, or selective estrogen receptor modulators, agents known in the art to prevent bone loss by inhibiting bone resorption via pathways believed to be similar to those of estrogens. These agents may be used in combination with the compounds of the present invention to beneficially treat bone disorders including osteoporosis. Such agents include, for example, tamoxifen, raloxifene, lasofoxifene, toremifene, azorxifene, EM-800, EM-652, TSE 424, clomiphene, droloxifene, idoxifene, and levormeloxifene [Goldstein, et al., "A pharmacological review of selective estrogen receptor modulators," *Human Reproduction Update*, 6: 212–224 (2000), and Lufkin, et al., "The role of selective estrogen receptor modulators in the prevention and treatment of osteoporosis," *Rheumatic Disease Clinics of North America*, 27: 163–185 (2001)]. SERMs are also discussed in "Targeting the Estrogen Receptor with SERMs," *Ann. Rep. Med. Chem.* 36: 149–158 (2001).

αvβ3 Integrin receptor antagonists suppress bone resorption and may be employed in combination with the tissue selective androgen receptor modulators of structural formula I for the treatment of bone disorders including osteoporosis. Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195–204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S. Pat. Nos. 5,204,350; 5,217,994; 5,639,754; 5,741,796; 5,780,426; 5,929,120; 5,952,341; 6,017,925; and 6,048,861. Evidence of the ability of αvβ3 integrin receptor antagonists to prevent bone resorption in vitro and in vivo has been presented (see V. W. Engleman et al., "A Peptidomimetic Antagonist of the αvβ3 Integrin Inhibits Bone Resorption In Vitro and Prevents Osteoporosis In Vivo," *J. Clin. Invest.* 99: 2284–2292 (1997); S. B. Rodan et al., "A High Affinity Non-Peptide αvβ3 Ligand Inhibits Osteoclast Activity In Vitro and In Vivo," *J. Bone Miner. Res.* 11: S289 (1996); J. F. Gourvest et al., "Prevention of OVX-Induced Bone Loss With a Non-peptidic Ligand of the αvβ3 Vitronectin Receptor," *Bone* 23: S612 (1998); M. W. Lark et al., "An Orally Active Vitronectin Receptor αvβ3 Antagonist Prevents Bone Resorption In Vitro and In Vivo in the Ovariectomized Rat," Bone 23: S219 (1998)). Other αvβ3 antagonists are described in R. M. Keenan et al., "Discovery of Potent Nonpeptide Vitronectin Receptor (αvβ3) Antagonists," *J. Med. Chem.* 40: 2289–2292 (1997); R. M. Keenan et al., "Benzimidazole Derivatives As Arginine Mimetics in 1,4-Benzodiazepine Nonpeptide Vitronectin Receptor (αvβ3) Antagonists," *Bioorg. Med. Chem. Lett.* 8: 3165–3170 (1998); and R. M. Keenan et al., "Discovery of an Imidazopyridine-Containing 1,4-Benzodiazepine Nonpeptide Vitronectin Receptor (αvβ3) Antagonist With Efficacy in a Restenosis Model," *Bioorg. Med. Chem. Lett.* 8: 3171–3176 (1998). Still other benzazepine, benzodiazepine and benzocycloheptene αvβ3 integrin receptor antagonists are described in the following patent publications: WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, WO 99/15506, and U.S. Pat. No. 6,159,964, and WO 97/34865. αvβ3 integrin receptor antagonists having dibenzocycloheptene, dibenzocycloheptane and dibenzoxazepine scaffolds have been described in WO 97/01540, WO 98/30542, WO 99/11626, WO 99/15508, WO 00/33838, U.S. Pat. Nos. 6,008,213, and 6,069,158. Other osteoclast integrin receptor antagonists incorporating backbone conformational ring constraints have been described in the patent literature. Published patent applications or issued patents disclosing antagonists having a phenyl constraint include WO 98/00395, WO 99/32457, WO 99/37621, WO 99/44994, WO 99/45927, WO 99/52872, WO 99/52879, WO 99/52896, WO 00/06169, EP 0 820,988, EP 0 820,991, U.S. Pat. Nos. 5,741,796; 5,773, 644; 5,773,646; 5,843,906; 5,852,210; 5,929,120; 5,952, 381; 6,028,223; and 6,040,311. Published patent applications or issued patents disclosing antagonists having a monocyclic ring constraint include WO 99/26945, WO 99/30709, WO 99/30713, WO 99/31099, WO 99/59992, WO 00/00486, WO 00/09503, EP 0 796,855, EP 0 928,790, EP 0 928,793, U.S. Pat. Nos. 5,710,159; 5,723,480; 5,981, 546; 6,017,926; and 6,066,648. Published patent applications or issued patents disclosing antagonists having a bicyclic ring constraint include WO 98/23608, WO 98/35949, WO 99/33798, EP 0 853,084, U.S. Pat. Nos. 5,760,028; 5,919,792; and 5,925,655. Reference is also made to the following reviews for additional scientific and patent literature that concern alpha v integrin antagonists: M. E. Duggan, et al., "Ligands to the integrin receptor αvβ3, *Exp. Opin. Ther. Patents,* 10: 1367–1383 (2000); M. Gowen, et al., "Emerging therapies for osteoporosis," *Emerging Drugs,* 5: 1–43 (2000); J. S. Kerr, et al., "Small molecule αv integrin antagonists: novel anticancer agents," *Exp. Opin. Invest. Drugs,* 9: 1271–1291 (2000); and W. H. Miller, et al., "Identification and in vivo efficacy of small-molecule antagonists of integrin αvβ3 (the vitronectin receptor)," *Drug Discovery Today,* 5: 397–408 (2000).

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (see *The Wall Street Journal*, Friday, Dec. 3, 1999, page B1). Therefore, the statins hold promise for the treatment of bone resorption. Examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), rosuvastatin, also known as ZD-4522 (see U.S. Pat. No. 5,260,440) and pitavastatin, also referred to as NK-104, itavastatin, or nisvastatin (see PCT international application publication number WO 97/23200).

Osteoclast vacuolar ATPase inhibitors, also called proton pump inhibitors, may also be employed together with the tissue selective androgen receptor modulators of structural formula I. The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases [see C. Farina et al., "Selective inhibitors of the osteoclast vacuolar proton ATPase as novel bone antiresorptive agents," *DDT,* 4: 163–172 (1999)].

The angiogenic factor VEGF has been shown to stimulate the bone-resorbing activity of isolated mature rabbit osteoclasts via binding to its receptors on osteoclasts [see M. Nakagawa et al., "Vascular endothelial growth factor (VEGF) directly enhances osteoclastic bone resorption and survival of mature osteoclasts," *FEBS Letters,* 473: 161–164 (2000)]. Therefore, the development of antagonists of VEGF binding to osteoclast receptors, such as KDR/Flk-1 and Flt-1, may provide yet a further approach to the treatment or prevention of bone resorption.

Activators of the peroxisome proliferator-activated receptor-γ (PPARγ), such as the thiazolidinediones (TZD's), inhibit osteoclast-like cell formation and bone resorption in vitro. Results reported by R. Okazaki et al. in *Endocrinology,* 140: 5060–5065 (1999) point to a local mechanism on bone marrow cells as well as a systemic one on glucose metabolism. Nonlimiting examples of PPARγ activators include the glitazones, such as troglitazone, pioglitazone, rosiglitazone, and BRL 49653.

Calcitonin may also be employed together with the tissue selective androgen receptor modulator of structural formula I. Calcitonin is preferentially employed as salmon nasal spray (Azra et al., Calcitonin. 1996. In: J. P. Bilezikian, et al., Ed., *Principles of Bone Biology*, San Diego: Academic Press; and Silverman, "Calcitonin," *Rheumatic Disease Clinics of North America*, 27: 187–196, 2001)

Protein kinase inhibitors may also be employed together with the tissue selective androgen receptor modulators of structural formula I. Kinase inhibitors include those disclosed in WO 01/17562 and are in one embodiment selected from inhibitors of p38. Specific embodiments of p38 inhibitors useful in the present invention include SB 203580 [Badger et al., "Pharmacological profile of SB 203580, a selective inhibitor of cytokine suppressive binding protein/p38 kinase, in animal models of arthritis, bone resorption, endotoxin shock, and immune function," *J. Pharmacol. Exp. Ther.*, 279: 1453–1461 (1996)].

Osteoanabolic agents are those agents that are known in the art to build bone by increasing the production of the bone protein matrix. Such osteoanabolic agents include, for example, the various forms of parathyroid hormone (PTH) such as naturally occurring PTH (1–84), PTH (1–34), analogs thereof, native or with substitutions and particularly parathyroid hormone subcutaneous injection. PTH has been found to increase the activity of osteoblasts, the cells that form bone, thereby promoting the synthesis of new bone (*Modern Drug Discovery*, Vol. 3, No. 8, 2000). In studies reported at the First World Congress on Osteoporosis held in Chicago in June 2000, women in combined PTH-estrogen therapy exhibited a 12.8% increase in spinal bone mass and a 4.4% increase in total hip mass. Another study presented at the same meeting showed that PTH could increase bone size as well as density. A clinical trial of the effect of the human parathyroid hormone 1–34 fragment [hPTH(1–34)] on postmenopausal osteoporotic women resulted in $\geq 65\%$ reduction in spine fractures and a 54% reduction in nonvertebral fractures, after a median of 22 months of treatment [see J. M. Hock, *Bone*, 27: 467–469 (2000) and S. Mohan, et al., *Bone*, 27: 471–478 (2000), and references cited therein]. Thus, PTH and fragments thereof, such as hPTH (1–34), may prove to be efficacious in the treatment of osteoporosis alone or in combination with other agents, such as the tissue selective androgen receptor modulators of the present invention. An injectable recombinant form of human PTH, Forteo (teriparatide), has received regulatory approval in the U.S. for the treatment of osteoporosis.

Also useful in combination with the SARMs of the present invention are calcium receptor antagonists which induce the secretion of PTH as described by Gowen et al., in "Antagonizing the parathyroid calcium receptor stimulates parathyroid hormone secretion and bone formation in osteopenic rats," *J. Clin. Invest.* 105: 1595–604 (2000).

Growth hormone secretagogues, growth hormone, growth hormone releasing hormone and the like are also osteoanabolic agents which may be employed with the compounds according to structural formula I for the treatment of osteoporosis. Representative growth hormone secretagogues are disclosed in U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent, Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; *Science*, 260, 1640–1643 (Jun. 11, 1993); *Ann. Rep. Med. Chem.*, 28: 177–186 (1993); *Bioorg. Med. Chem. Lett.*, 4: 2709–2714 (1994); and *Proc. Natl. Acad. Sci. USA*, 92: 7001–7005 (1995).

Insulin-like growth factor (IGF) may also be employed together with the tissue selective androgen receptor modulators of structural formula I. Insulin-like growth factors may be selected from Insulin-like Growth Factor I, alone or in combination with IGF binding protein 3 and IGF II [See Johannson and Rosen, "The IGFs as potential therapy for metabolic bone diseases," 1996, In: Bilezikian, et al., Ed., *Principles of Bone Biology*, San Diego: Academic Press; and Ghiron et al., "Effects of recombinant insulin-like growth factor-I and growth hormone on bone turnover in elderly women," *J. Bone Miner. Res.* 10: 1844–1852 (1995)].

Bone morphogenetic protein (BMP) may also be employed together with the tissue selective androgen receptor modulators of structural formula I. Bone morphogenetic protein includes BMP 2, 3, 5, 6, 7, as well as related molecules TGF beta and GDF 5 [Rosen et al., "Bone morphogenetic proteins," 1996. In: J. P. Bilezikian, et al., Ed., *Principles of Bone Biology*, San Diego: Academic Press; and Wang EA, "Bone morphogenetic proteins (BMPs): therapeutic potential in healing bony defects," *Trends Biotechnol.*, 11: 379–383 (1993)].

Inhibitors of BMP antagonism may also be employed together with the tissue selective androgen receptor modulators of structural formula I. BMP antagonist inhibitors are in one embodiment selected from inhibitors of the BMP antagonists SOST, noggin, chordin, gremlin, and dan [Massague and Chen, "Controlling TGF-beta signaling," *Genes Dev.*, 14: 627–644, 2000; Aspenberg et al., "The bone morphogenetic proteins antagonist Noggin inhibits membranous ossification," *J. Bone Miner. Res.* 16: 497–500, 2001; Brunkow et al., "Bone dysplasia sclerosteosis results from loss of the SOST gene product, a novel cystine knot-containing protein," *Am. J. Hum. Genet.* 68: 577–89 (2001)].

The tissue-selective androgen receptor modulators of the present invention may also be combined with the polypeptide osteoprotegerin for the treatment of conditions associated with bone loss, such as osteoporosis. Preferably osteoprotegerin is mammalian osteoprotegerin and more preferably human osteoprotegerin. The polypeptide osteoprotegerin, a member of the tumor necrosis factor receptor superfamily, is useful to treat bone diseases characterized by increased bone loss, such as osteoporosis. Reference is made to U.S. Pat. No. 6,288,032, which is incorporated by reference herein in its entirety.

Prostaglandin derivatives may also be employed together with the tissue selective androgen receptor modulators of structural formula I. Prostaglandin derivatives are in one embodiment selected from agonists of prostaglandin receptor EP1, EP2, EP4, FP and IP or a derivative thereof [Pilbeam et al., "Prostaglandins and bone metabolism," 1996. In: Bilezikian, et al. Ed. Principles of Bone Biology, San Diego: Academic Press; Weinreb et al., "Expression of the prostaglandin E(2) (PGE(2)) receptor subtype EP(4) and its regulation by PGE(2) in osteoblastic cell lines and adult rat bone tissue," Bone, 28: 275–281 (2001)].

Fibroblast growth factors may also be employed together with the tissue selective androgen receptor modulators of structural formula I. Fibroblast growth factors include aFGF, bFGF and related peptides with FGF activity [Hurley Florkiewicz, "Fibroblast growth factor and vascular endothelial growth factor families," 1996. In: J. P. Bilezikian, et al., Ed. Principles of Bone Biology, San Diego: Academic Press].

In addition to bone resorption inhibitors and osteoanabolic agents, there are also other agents known to be beneficial for the skeleton through mechanisms which are not precisely defined. These agents may also be favorably combined with the tissue selective androgen receptor modulators of structural formula I.

Vitamin D and vitamin D derivatives may also be employed together with the tissue selective androgen receptor modulator of structural formula I. Vitamin D and vitamin D derivatives include natural vitamin D, 25-OH-vitamin D3, $1\alpha,25(OH)_2$ vitamin D3, $1\alpha$-OH-vitamin D3, $1\alpha$-OH-vitamin D2, dihydrotachysterol, $26,27$-$F6$-$1\alpha,25(OH)_2$ vitamin D3, $19$-nor-$1\alpha,25(OH)_2$ vitamin D3, 22-oxacalcitriol, calcipotriol, $1\alpha,25(OH)_2$-16-ene-23-yne-vitamin D3 (Ro 23-7553), EB1089, 20-epi-$1\alpha,25(OH)_2$ vitamin D3, KH1060, ED71, $1\alpha,24(S)$—$(OH)_2$ vitamin D3, $1\alpha,24(R)$—$(OH)_2$ vitamin D3 [See, Jones G., "Pharmacological mechanisms of therapeutics: vitamin D and analogs," 1996. In: J. P. Bilezikian, et . al. Ed. Principles of Bone Biology, San Diego: Academic Press].

Vitamin K and vitamin K derivatives may also be employed together with the tissue selective androgen receptor modulators of structural formula I. Vitamin K and vitamin K derivatives include menatetrenone (vitamin K2) [see Shiraki et al., "Vitamin K2 (menatetrenone) effectively prevents fractures and sustains lumbar bone mineral density in osteoporosis," J. Bone Miner. Res., 15: 515–521 (2000)].

Soy isoflavones, including ipriflavone, may be employed together with the tissue selective androgen receptor modulators of structural formula I.

Fluoride salts, including sodium fluoride (NaF) and monosodium fluorophosphate (MFP), may also be employed together with the tissue selective androgen receptor modulators of structural formula I. Dietary calcium supplements may also be employed together with the tissue selective androgen receptor modulators of structural formula I. Dietary calcium supplements include calcium carbonate, calcium citrate, and natural calcium salts (Heaney. Calcium. 1996. In: J. P. Bilezikian, et al., Ed., Principles of Bone Biology, San Diego: Academic Press).

Daily dosage ranges for bone resorption inhibitors, osteoanabolic agents and other agents which may be used to benefit the skeleton when used in combination with a compound of structural formula I are those which are known in the art. In such combinations, generally the daily dosage range for the tissue selective androgen receptor modulator of structural formula I is 0.01 to 1000 mg per adult human per day, more preferably from 0.1 to 200 mg/day. However, adjustments to decrease the dose of each agent may be made due to the increased efficacy of the combined agent.

In particular, when a bisphosphonate is employed, dosages of 2.5 to 100 mg/day (measured as the free bisphosphonic acid) are appropriate for treatment, more preferably 5 to 20 mg/day, especially about 10 mg/day. Prophylactically, doses of about 2.5 to about 10 mg/day and especially about 5 mg/day should be employed. For reduction in side-effects, it may be desirable to administer the combination of a compound of structural formula I and the bisphosphonate once a week. For once weekly administration, doses of about 15 mg to 700 mg per week of bisphosphonate and 0.07 to 7000 mg of a compound of structural formula I may be employed, either separately, or in a combined dosage form. A compound of structural formula I may be favorably administered in a controlled-release delivery device, particularly for once weekly administration.

For the treatment of atherosclerosis, hypercholesterolemia, and hyperlipidemia, the compounds of structural formula I may be effectively administered in combination with one or more additional active agents. The additional active agent or agents can be lipid-altering compounds such as HMG-CoA reductase inhibitors, or agents having other pharmaceutical activities, or agents that have both lipid-altering effects and other pharmaceutical activities. Examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), and nisvastatin, also referred to as NK-104 (see PCT international application publication number WO 97/23200). Additional active agents which may be employed in combination with a compound of structural formula I include, but are not limited to, HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors, such as SCH-58235, also known as ezetimibe and 1-(4-fluorophenyl)-3(R)-[3(S)-(4-fluorophenyl)-3-hydroxypropyl)]-4(S)-(4-hydroxyphenyl)-2-azetidinone, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and, including those compounds included within the structural class known as thiazolidinediones as well as those PPARγ agonists outside the thiazolidinedione structural class; PPARα agonists, such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors, such as enalapril and captopril; calcium channel blockers, such as nifedipine and diltiazem; endothelin antagonists; agents such as LXR ligands that enhance ABC1 gene expression; bisphosphonate compounds, such as alendronate sodium; and cyclooxygenase-2 inhibitors, such as rofecoxib and celecoxib, as well as other agents known to be useful in the treatment of these conditions.

Daily dosage ranges for HMG-CoA reductase inhibitors when used in combination with the compounds of structural formula I correspond to those which are known in the art. Similarly, daily dosage ranges for the HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors including ezetimibe; bile acid sequestrants; LDL (low density lipoprotein) receptor inducers; platelet aggregation inhibitors, including glycoprotein IIb/IIIa fibrinogen receptor antagonists and aspirin; human peroxisome proliferator activated receptor gamma (PPARγ) agonists; PPARα agonists; PPAR dual α/γ agonists; vitamin $B_6$; vitamin $B_{12}$; folic acid; anti-oxidant vitamins; beta-blockers; angiotensin II antagonists; angiotensin converting enzyme inhibitors; calcium channel blockers; endothelin antagonists; agents such as LXR ligands that enhance ABC1 gene expression; bisphosphonate compounds; and cyclooxygenase-2 inhibitors also correspond to those which are known in the art, although due to the combined action with the compounds of structural formula I, the dosage may be somewhat lower when administered in combination.

One embodiment of the invention is a method for effecting a bone turnover marker in a mammal comprising administering a therapeutically effective amount of a compound according to formula I. Non-limiting examples of bone turnover markers can be selected from urinary C-telopeptide degradation products of type I collagen (CTX), urinary N-telopeptide cross-links of type I collagen (NTX), DXA, and DPD.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating diseases caused by androgen deficiency or that can be ameliorated by addition of androgen.

Abbreviations Used in the Description of the Preparation of the Compounds of the Present Invention:

| AcOH | Acetic acid |
| BOP | Benzotriazol-1-yloxytris(dimethylamino)phosphonium hexafluorophosphate |
| Bu | Butyl |
| calc. | Calculated |
| $CH_2Cl_2$ | Methylene chloride |
| CBZ(Cbz) | Benzyloxycarbonyl |
| $Cs_2CO_3$ | Cesium carbonate |
| DDQ | 2,3-Dichloro-5,6-dicyano-1,4-benzoquinone |
| DEAD | Diethyl azodicarboxylate |
| DIBAL | Diisobutylaluminum hydride |
| DIEA | Diisopropylethylamine |

-continued

| DMAP | 4-Dimethylaminopyridine |
| DMF | N,N-Dimethylformamide |
| DMSO | Dimethyl sulfoxide |
| EDC | 1-(3-Dimethylaminopropyl)3-ethylcarbodiimide HCl |
| ES-MS | Electron-spray mass spectroscopy |
| Et | ethyl |
| $Et_2O$ | Diethyl ether |
| $Et_3N$ | Triethylamine |
| EtOAc | Ethyl acetate |
| FAB | Fast atom bombardment |
| $FN(SO_2Ph)_2$ | N-Fluorobenzenesulfonimide |
| HOAt | 1-Hydroxy-7-azabenzotriazole |
| HOBt | N-hydroxybenzotriazole |
| HPLC | High-performance liquid chromatography |
| HRMS | High resolution mass spectrum |
| i-PrOH | Isopropyl alcohol |
| LAH | Lithium aluminum hydride |
| LDA | Lithium diisopropylamide |
| Me | Methyl |
| MF | molecular formula |
| $MgSO_4$ | Magnesium sulfate |
| MS | mass spectrum |
| NMM | N-methylmorpholine |
| $Na_2SO_4$ | Sodium sulfate |
| Ph | Phenyl |
| PhS(O)OMe | Methyl benzenesulfinate |
| Pr | Propyl |
| r.t. | Room temperature |
| $NaHCO_3$ | Sodium hydrogencarbonate |
| TFA | Trifluoroacetic acid |
| THF | Tetrahydrofuran |
| TLC | Thin-layer chromatography. |

Preparation of the Compounds of the Invention

The compounds of the present invention can be prepared according to the procedures denoted in the following reaction Schemes and Examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

The selective androgen receptor modulators (SARMs) of structural formula 1–5 were prepared as outlined in Scheme 1. The starting material was the 17β-carboxylate 1-1 which is disclosed in G. H. Rasmusson et al., *J. Med. Chem.*, 27: 1690–1701 (1984).

Scheme 1

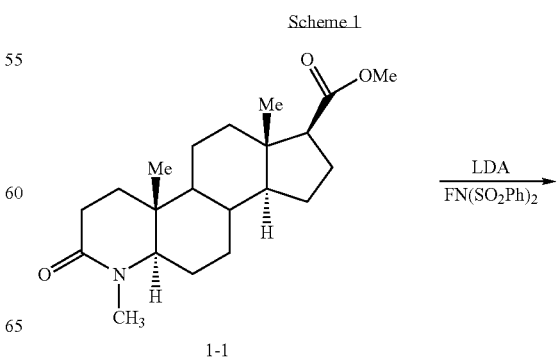

1-1

-continued
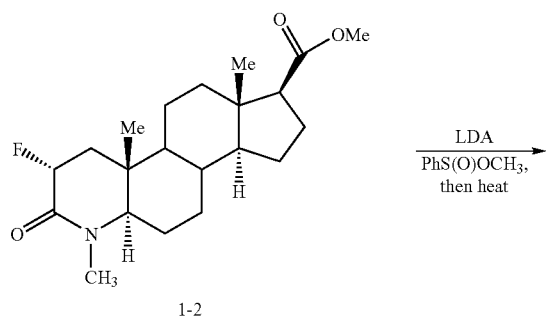
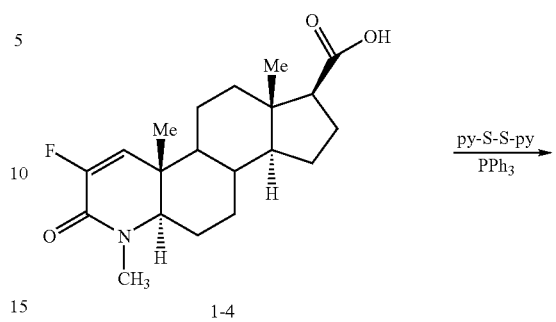
Scheme 2
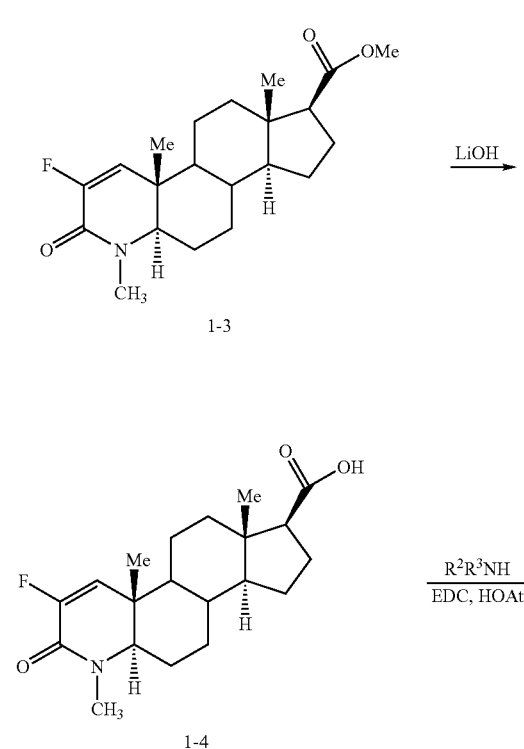
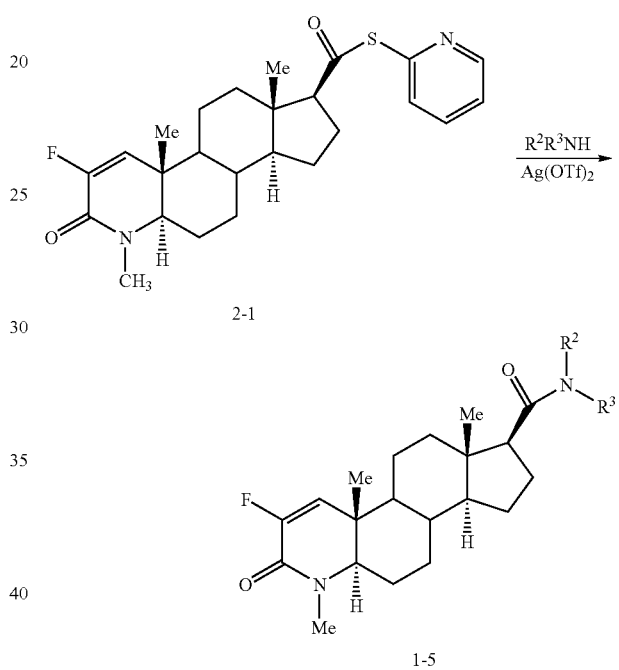
Alternatively the compounds of structural formula 1-5 were prepared from intermediate 1-3 as shown in Scheme 2:
Compounds of structural formula 3-6 in Scheme 3 were prepared as outlined in Scheme 3 below. The starting material was the 17β-carboxylic acid 3-1 which is disclosed in G. H. Rasmusson et al., *J. Med. Chem.*, 29: 2298–2315 (1986) and R. L. Tolman, et al., *J. Steroid Biochem. Mol. Biol.*, 60: 303–309 (1997).
Scheme 3
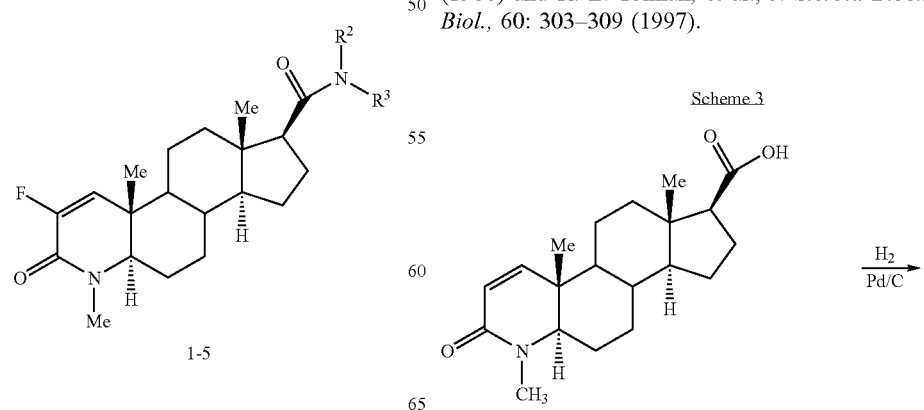

-continued

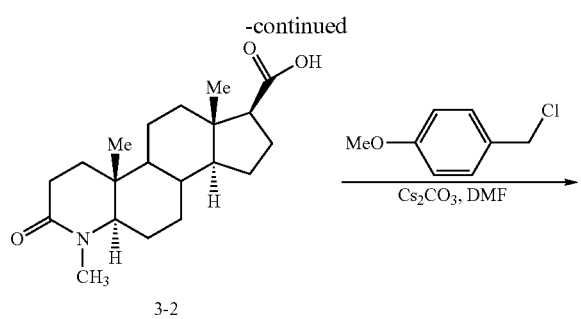

3-2

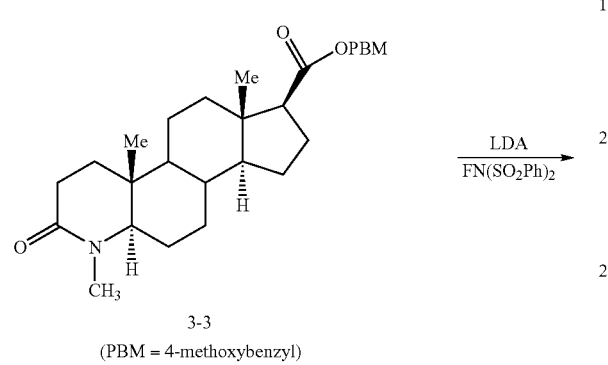

3-3
(PBM = 4-methoxybenzyl)

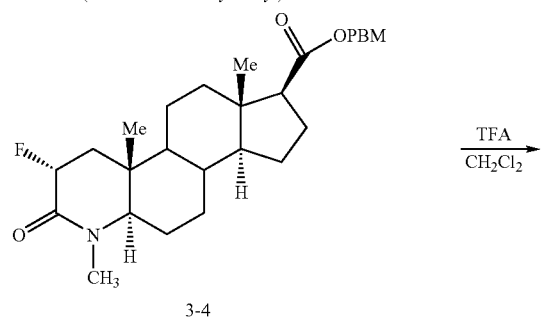

3-4

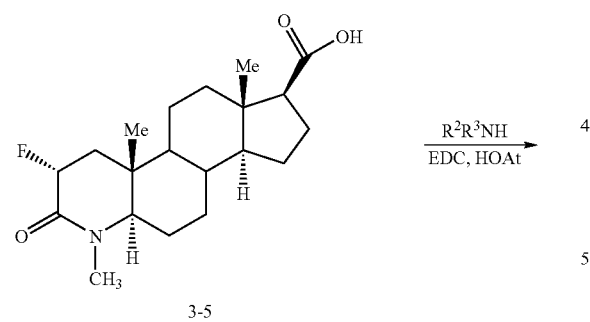

3-5

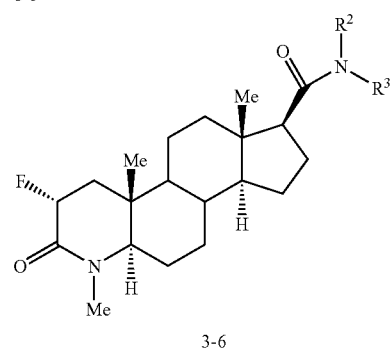

3-6

Alternatively the compounds of structural formula 3-6 were prepared from intermediate 3-5 as shown in Scheme 4:

Scheme 4

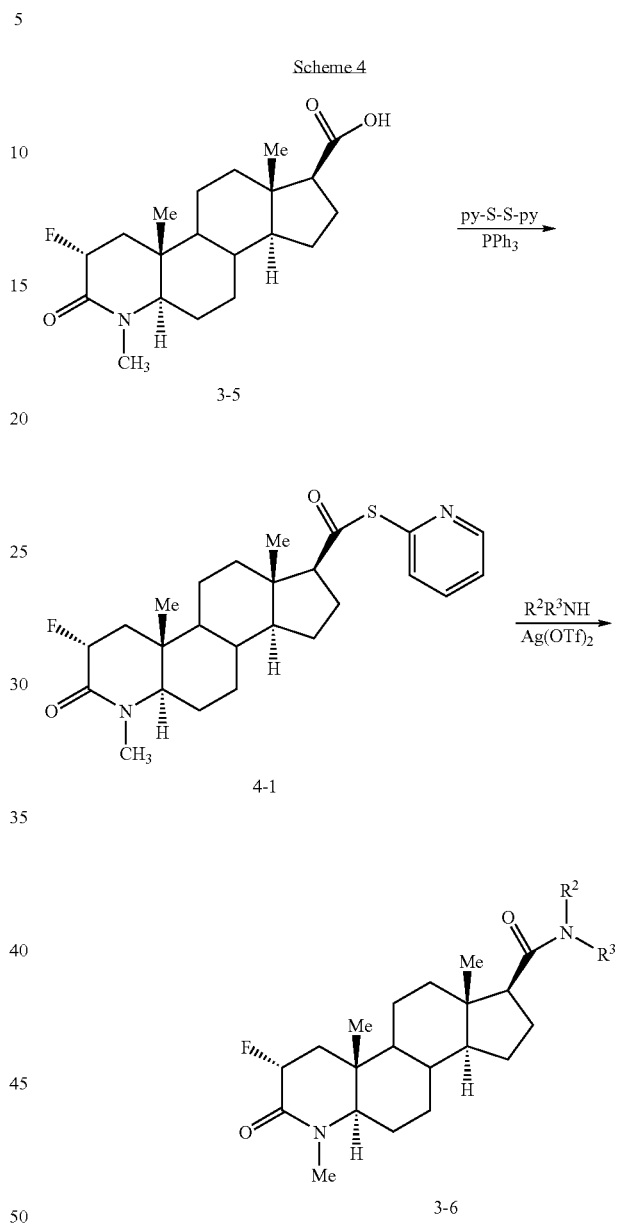

The following examples are provided to further illustrate details for the preparation and use of the compounds of the present invention. They are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Scheme 5

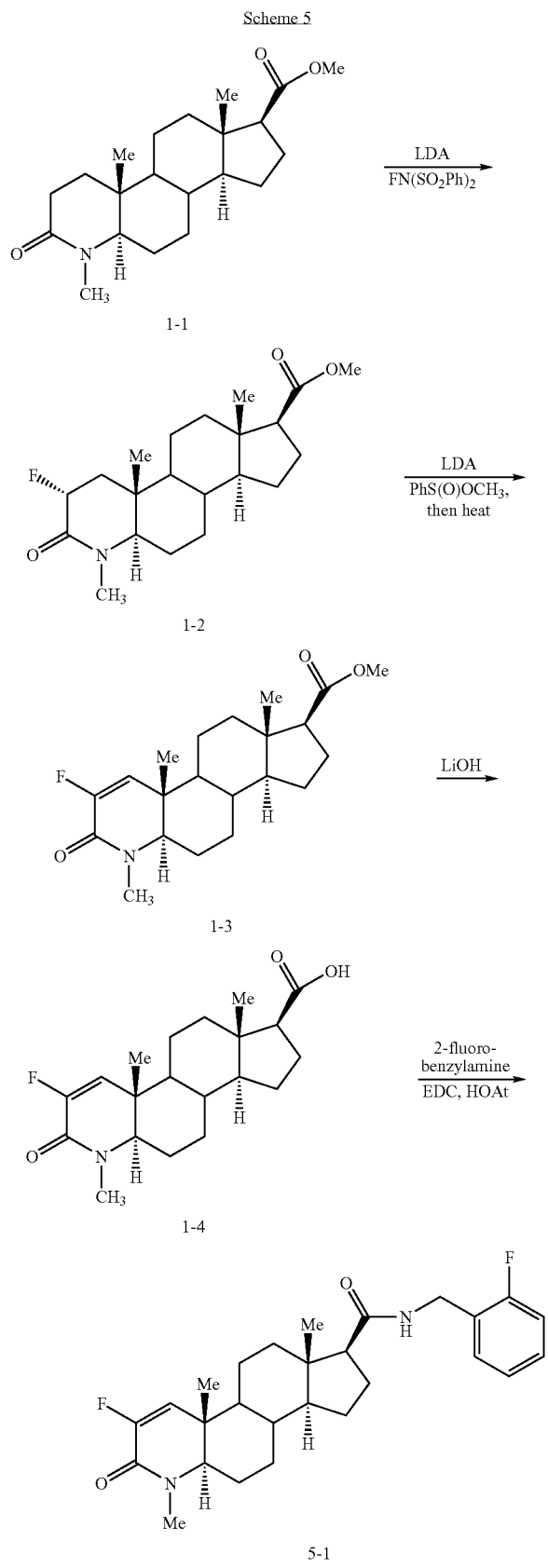

EXAMPLE 1

Step A: 2α-Fluoro-4-methyl-3-oxo-4-aza-5α-androstane-17β-carboxylic Acid Methyl Ester (1-2)

To a solution of 1-1 (7.5 g, 21.6 mmol) in THF (100 mL) at −78° C. was added a solution of 1.5 M LDA in THF (17.3 mL, 25.9 mmol) dropwise over 20 min and then stirred 1 h. A solution of FN(SO$_2$Ph)$_2$ (10.2 g, 32.4 mmol) in THF (40 mL) was then added over 20 min. After 30 min, the cooling bath was removed and the reaction was stirred for 14 h. Et$_2$O was added, and the mixture was washed with water, saturated aqueous sodium hydrogencarbonate, brine, dried (MgSO$_4$) and then concentrated. Chromatography on silica gel (hexanes to EtOAc as eluent) gave 1-2 (4.2 g) as a colorless solid.

MS calculated M+H: 366. Found 366.1.

Step B: 2-Fluoro-4-methyl-3-oxo-4-aza-5α-androst-1-ene-17β-carboxylic Acid Methyl Ester (1-3)

To a solution of 1-2 (30 g, 82.1 mmol) in THF (400 mL) at −78° C. was added a solution of 1.5 M LDA in THF (71.1 mL, 107 mmol) dropwise over 30 min and then stirred 1 h. Methyl benzenesulfinate (19.23 g, 123 mmol) was then added over 15 min. After 30 min, the cooling bath was removed and the reaction was stirred for 1 h. Et$_2$O was added, and the mixture was washed with water, saturated aqueous sodium hydrogencarbonate, brine, dried (MgSO$_4$) and then concentrated. The residue was dissolved in toluene (200 mL) and heated at reflux for 2 h. Solvent evaporation and chromatography of the residue on silica gel (hexanes to 50% EtOAc/hexanes as eluent) gave 1-3 (20.4 g) as a pale yellow solid.

MS calculated M+H: 364. Found 364.1.

Step C: 2-Fluoro-4-methyl-3-oxo-4-aza-5α-androst-1-ene-17β-carboxylic Acid (1-4)

To a solution of 1-3 (2.4 g, 6.6 mmol) in 1,4-dioxane (50 mL) was added a solution of lithium hydroxide (0.41 g, 9.9 mmol) in water (20 mL), and the mixture heated at 100° C. for 3 h. After cooling, the mixture was diluted with ethyl acetate and then washed with 1N HCl, brine, dried (MgSO$_4$) and then concentrated to give 1-4 (2.2 g) as a pale yellow solid.

MS calculated M+H: 350. Found 350.

Step D: N-(2-fluorophenylmethyl)-2-fluoro-4-methyl-3-oxo-4-aza-5α-androst-1-en-17β-carboxamide (5-1)

A mixture of 1-4 (0.12 g, 0.34 mmol), EDC (0.079 g, 0.41 mmol), HOAt (0.056 g, 0.41 mmol), NMM (0.15 mL, 1.37 mmol) and 2-fluorobenzylamine (0.52 g, 0.41 mmol) in DMF (2 mL) stirred for 14 h. The mixture was diluted with water, filtered, and the solids washed with water, then diethyl ether, and then dried under vacuum to give 5-1 (0.12 g) as a pale yellow solid.

MS calculated M+H: 457.2661. Found 457.2666.

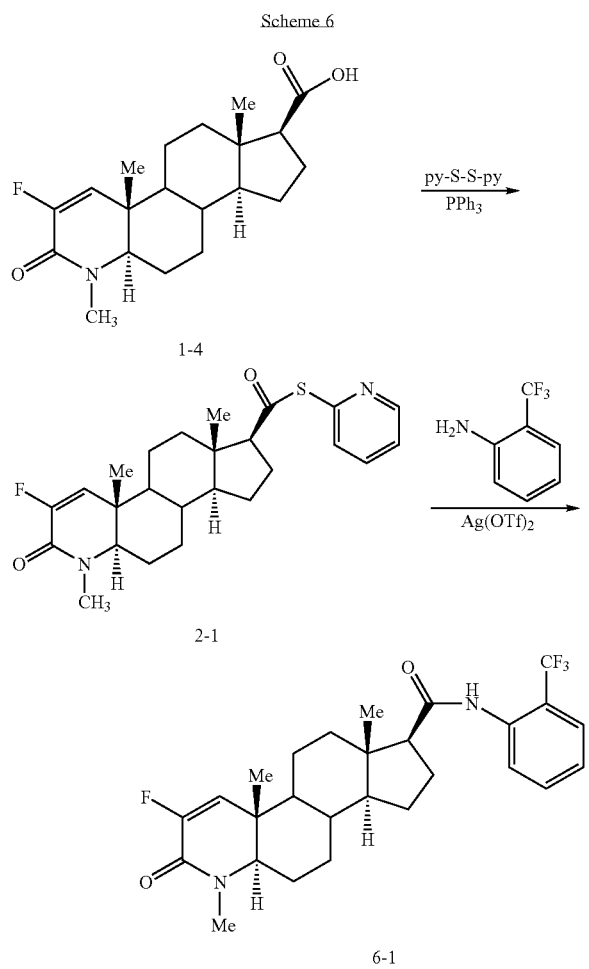

Scheme 6

EXAMPLE 2

Step A: S-(Pyridin-2-yl)-2-fluoro-4-methyl-3-oxo-4-aza-5α-androst-1-en-17β-carbothioate (2-1)

A mixture of 1-4 (0.80 g, 2.30 mmol), 2,2'-dithiopyridine (1.01 g, 4.6 mmol) and triphenylphosphine (1.2 g, 4.6 mmol) in toluene (10 mL) was stirred 14 h. Following evaporation of the solvent, the solids were suspended in toluene (5 mL) and diluted with diethyl ether. The solids were collected by filtration, washed with diethyl ether, and then dried under vacuum to give 2-1 (0.12 g) as a pale yellow solid.

MS calculated M+H: 443. Found 443.

Step B: N-(2-Trifluoromethylphenyl)-2-fluoro-4-methyl-3-oxo-4-aza-5α-androst-1-en-17β-carboxamide (6-1)

A mixture of 2-1 (0.25 g, 0.57 mmol), 2-trifluoromethylaniline (0.18 g, 1.13 mmol) and silver(II) triflate (0.15 g, 0.57 mmol) in dichloromethane (3 mL) was stirred 14 h. Following evaporation of the solvent, chromatography of the residue on silica gel (hexanes to EtOAc as eluent) gave 6-1 (0.12 g) as a pale yellow solid.

MS calculated M+H: 493.2473. Found 493.2470.

Examples 3–50 in Table 1 were prepared in a similar manner as Examples 1 and 2, but using the appropriate amine to generate the carboxamide.

TABLE 1

| Ex. | $NR^2R^3$ | Mass spectrum Measured [M + H] |
|---|---|---|
| 3 | HN—CH2—C6H4—F (3-fluorobenzyl) | 457.2663 |
| 4 | HN—C6H4—Cl (2-chlorophenyl) | 459.2205 |
| 5 | HN—(pyridin-2-yl)—CH3 | 440.2747 |
| 6 | HN—CH2—C6H4—F (4-fluorobenzyl) | 4572645 |
| 7 | HN—CH2—(furan-2-yl) | 429.2536 |
| 8 | HN—CH2—(thiophen-2-yl) | 445.2302 |
| 9 | HN—CH2—C6H4—CF3 (2-trifluoromethylbenzyl) | 507.2637 |
| 10 | HN—CH2—(1H-benzimidazol-2-yl) | 479.2829 |
| 11 | HN—CH2—(1-methyl-benzimidazol-2-yl) | 493.2966 |

TABLE 1-continued
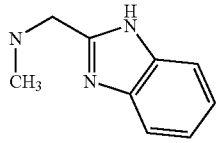
| Ex. | NR²R³ | Mass spectrum Measured [M + H] |
|---|---|---|
| 12 | 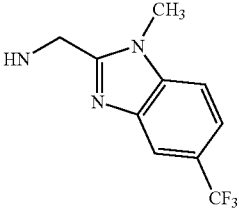 | 493.2175 |
| 13 | 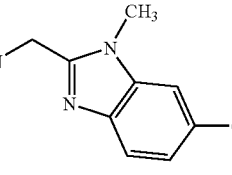 | 5612873 |
| 14 | 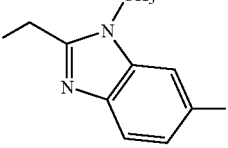 | 5132450 |
| 15 | 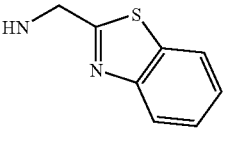 | 509.2947 |
| 16 | 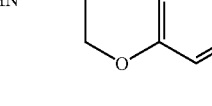 | 496.2410 |
| 17 | 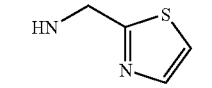 | 497.2825 |
| 18 | 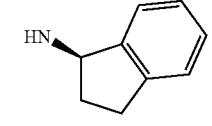 | 446.2278 |
TABLE 1-continued
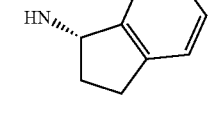
| Ex. | NR²R³ | Mass spectrum Measured [M + H] |
|---|---|---|
| 19 | 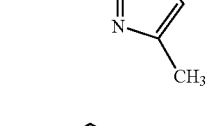 | 465.2910 |
| 20 | 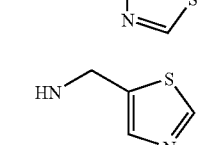 | 465.2911 |
| 21 | 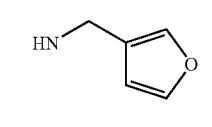 | 460.2436 |
| 22 | 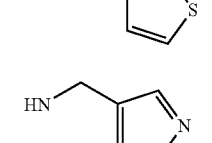 | 446.2274 |
| 23 | 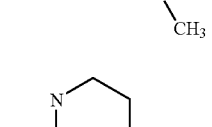 | 446.2274 |
| 24 | 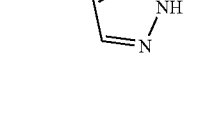 | 429.2555 |
| 25 | | 445.2319 |
| 26 | | 443.2815 |
| 27 | | 455.2826 |

TABLE 1-continued
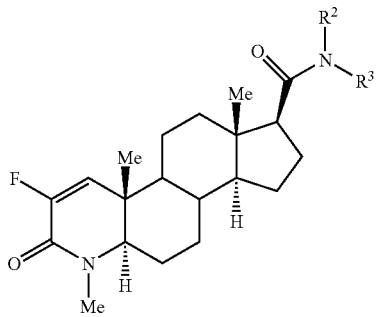
| Ex. | NR²R³ | Mass spectrum Measured [M + H] |
|---|---|---|
| 28 | HN-CH₂-(1-methylimidazol-2-yl) | 443.2809 |
| 29 | HN-CH₂-(oxazol-2-yl) | 430.2509 |
| 30 | HN-CH₂CF₃ | 431.2325 |
| 31 | HN-(2-CF₃-4-Cl-phenyl) | 527.2061 |
| 32 | HN-(4-OCH₃-phenyl) | 455.2714 |
| 33 | HN-(3-OCH₃-phenyl) | 439.2750 |
| 34 | HN-(2-CH₃-phenyl) | 439.2750 |
| 35 | HN-(3-CH₃-phenyl) | 439.2754 |
| 36 | HN-phenyl | 425.2611 |
TABLE 1-continued
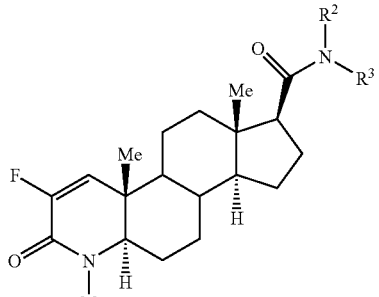
| Ex. | NR²R³ | Mass spectrum Measured [M + H] |
|---|---|---|
| 37 | HN-(2-F-phenyl) | 443.2503 |
| 38 | HN-(3-F-phenyl) | 443.2505 |
| 39 | HN-(4-F-phenyl) | 443.2504 |
| 40 | HN-(2-F-4-Cl-phenyl) | 477.2114 |
| 41 | HN-(2,4-diF-phenyl) | 461.2420 |
| 42 | HN-CH(CH₃)-phenyl (R) | 453.2920 |
| 43 | HN-CH(CH₃)-phenyl (S) | 453.2920 |
| 44 | HN-CH₂-(tetrahydropyran-2-yl) | 447.3032 |

TABLE 1-continued
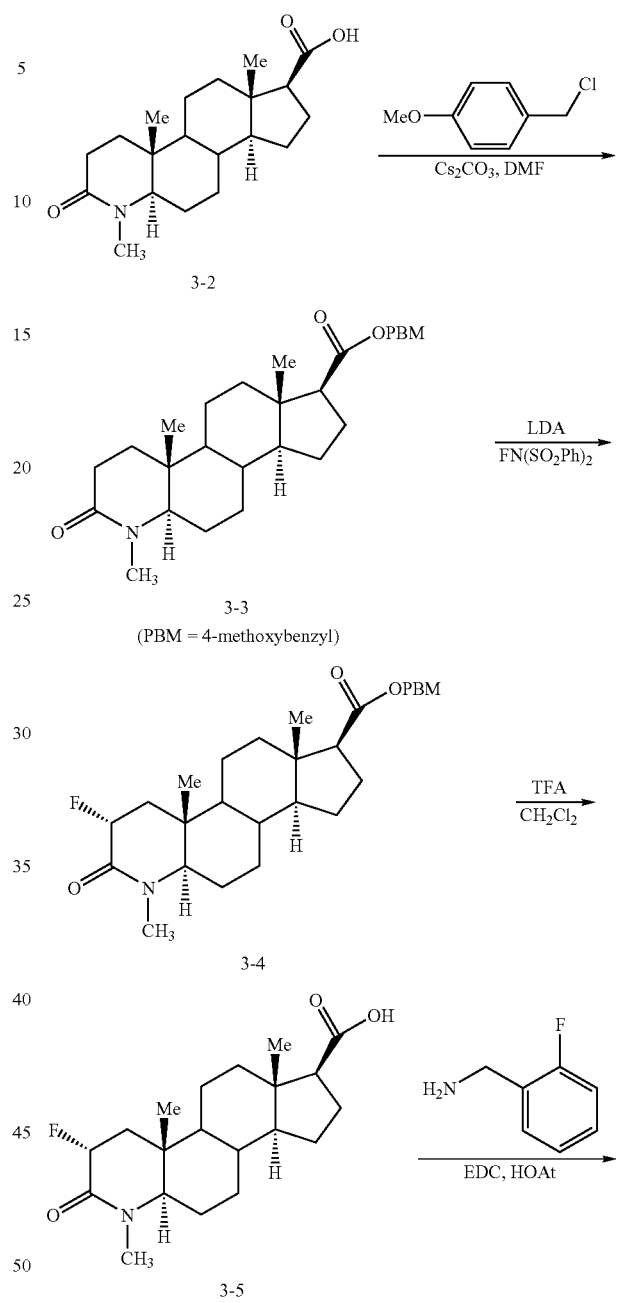
| Ex. | NR²R³ | Mass spectrum Measured [M + H] |
|---|---|---|
| 45 | HN-CH(H)-tetrahydropyran | 447.3043 |
| 46 | HN-CH(H)-benzodioxane | 497.2813 |
| 47 | HN-CH(H)-benzodioxane | 497.2795 |
| 48 | HN-CH(H)-tetrahydrofuran | — |
| 49 | HN-CH(H)-tetrahydrofuran | 433.2849 |
| 50 | HN-CH₂-imidazopyridine | 480.2763 |
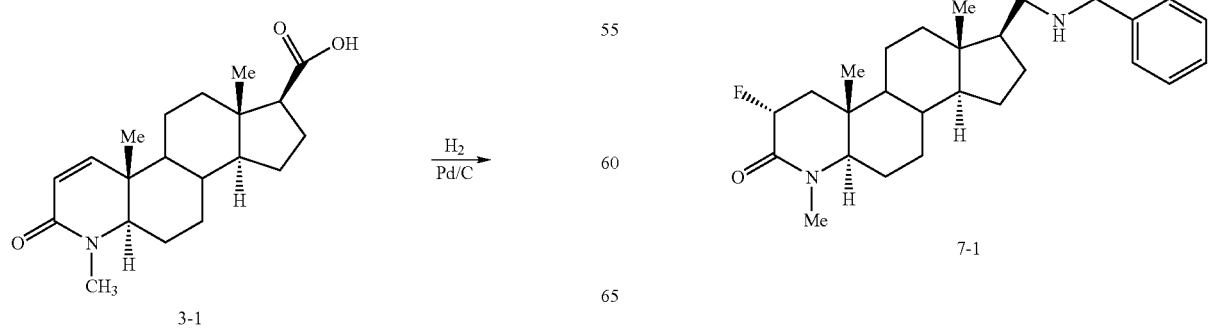

EXAMPLE 51

Step A: 4-Methyl-3-oxo-4-aza-5α-androstane-17β-carboxylic Acid (3-2)

To a suspension of 3-1 (13.2 g, 39.82 mmol) and EtOH (200 ml) was added LiOH (2 g, 47.8 mmol, dissolved in 20 ml H$_2$O). To the solution was added 10% Pd/C (1 g) and then the mixture was stirred under 1 atm H$_2$ for 4.0 hours. The reaction was filtered through a celite pad and then concentrated. To the residue was added 1N HCl. The solid that formed was collected, washed with Et$_2$O and then dried under vacuum to give 3-2 (10.5 g) as a white solid.

Step B: 4-Methyl-3-oxo-4-aza-5α-androstane-17β-carboxylic Acid 4-methoxybenzyl Ester (3-3)

To a suspension of 3-2 (10.5 g, 31.48 mmol) and DMF (200 ml) was added Cs$_2$CO$_3$ (10 g, 47.8 mmol) and 4-methoxybenzyl chloride (5.9 g, 37.78 mmol). The mixture was heated to 60° C. overnight. EtOAc was added, and the mixture was washed with 1N HCl, brine, dried (MgSO$_4$) and concentrated. The residue was triturated with EtOAc and then filtered. The solution was concentrated and the residue subjected to chromatography on silica gel (hexanes to EtOAc as eluent) to give 3-3 (7.22 g) as a white solid.

MS calculated M+H: 454.6. Found 454.3.

Step C: 2α-Fluoro-4-methyl-3-oxo-4-aza-5α-androst-1-ene-17β-carboxylic Acid 4-methoxybenzyl Ester (3-4)

To a solution of 3-3 (7.2 g, 15.9 mmol) in THF (100 mL) at −78° C. was added a solution of 1.5 M LDA in THF (12.7 mL, 19.05 mmol) dropwise over 20 min and then stirred for 1 h. A solution of FN(SO$_2$Ph)$_2$ (6.0 g, 19.05 mmol) in THF (40 mL) was then added over 20 min. After 30 min, the cooling bath was removed and the reaction was stirred for 14 h. Et$_2$O was added and then washed with water, saturated aqueous sodium hydrogencarbonate, brine, dried (MgSO$_4$) and then concentrated. Chromatography on silica gel (hexanes to EtOAc as eluent) gave 3-4 (3.1 g) as a colorless solid.

MS calculated M+H: 472.6. Found 472.3.

Step D: 2α-Fluoro-4-methyl-3-oxo-4-aza-5α-androst-1-ene-17β-carboxylic Acid (3-5)

To a solution of 3-4 (3.1 g, 6.57 mmol) in CH$_2$Cl$_2$ (20 ml) was added TFA (10 ml). After 30 minutes, the solution was concentrated and then azeotroped with toluene. The residue was dissolved in CH$_2$Cl$_2$ and then washed with 1N HCl, brine, dried (MgSO$_4$) and then concentrated to give 3-5 (2.1 g) as white solid.

MS calculated M+H: 352.5. Found 352.2.

Step E: N-(2-Fluorophenylmethyl)-2-fluoro-4-methyl-3-oxo-4-aza-5α-androstane-17β-carboxamide (7-1)

A mixture of 3-5 (0.10 g, 0.285 mmol), EDC (0.066 g, 0.34 mmol), HOAt (0.047 g, 0.34 mmol), NMM (0.13 mL, 1.14 mmol) and 2-fluorobenzylamine (0.52 g, 0.41 mmol) in DMF (2 mL) stirred for 14 h. The mixture was diluted with water, filtered, and the solids washed with water, then diethyl ether, and then dried under vacuum to give 7-1 (0.12 g) as a pale yellow solid.

MS calculated M+H: 459.2818. Found 459.2812.

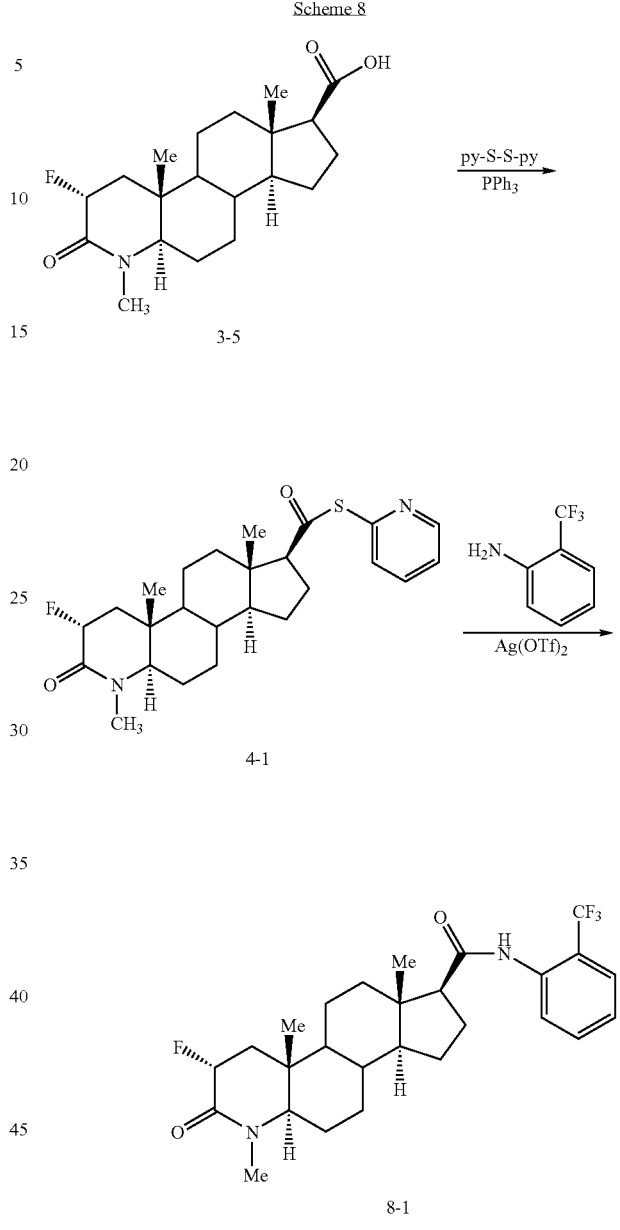

Scheme 8

EXAMPLE 52

Step A: S-(Pyridin-2-yl)-2α-fluoro-4-methyl-3-oxo-4-aza-5α-androstane-17β-carbothioate (4-1)

Utilizing the procedure described in Scheme 4, 4-1 was prepared from 3-5. MS calculated M+H: 445. Found 445.1.

Step B: N-(2-Trifluorophenyl)-2α-fluoro-4-methyl-3-oxo-4-aza-5α-androstane-17β-carboxamide (8-1)

Utilizing the procedure described in Scheme 4, 8-1 was prepared from 4-1. MS found M+H: 495.2624.

Examples 53–67 in Table 2 were prepared in a similar manner as Examples 51 and 52, but using the appropriate amine to generate the carboxamide.

TABLE 2

[Structure: steroidal scaffold with 2α-F, N-Me lactam (A-ring), and 17β-C(=O)NR³R⁴ carboxamide, with Me groups at C-13 and C-10]

| Ex. | NR³R⁴ | Mass spectrum Measured [M + H] |
|---|---|---|
| 53 | HN-CH₂-(3-F-phenyl) | 459.2811 |
| 54 | HN-CH₂-(4-F-phenyl) | 459.2807 |
| 55 | HN-CH₂-(1H-benzimidazol-2-yl) | 481.2970 |
| 56 | HN-CH₂-(1-methyl-benzimidazol-2-yl) | 495.3122 |
| 57 | HN-CH₂-CF₃ | 433.2478 |
| 58 | HN-CH₂-(thiazol-2-yl) | 448.2433 |
| 59 | HN-CH₂-(furan-2-yl) | 431.2715 |
| 60 | HN-CH₂-(thiophen-2-yl) | 447.2479 |
| 61 | HN-CH₂-(2-CF₃-phenyl) | 509.2786 |
| 62 | HN-(3-OCH₃-phenyl) | 457.2874 |

TABLE 2-continued

[Structure: similar scaffold but without C-14 H stereochemistry marker variant]

| Ex. | NR³R⁴ | Mass spectrum Measured [M + H] |
|---|---|---|
| 63 | HN-(4-OCH₃-phenyl) | 457.2873 |
| 64 | HN-(2-Cl-phenyl) | 461.2374 |
| 65 | HN-(2-CF₃-4-Cl-phenyl) | 386.957 |
| 66 | HN-CH(CH₃)-phenyl | 455.3082 |
| 67 | HN-CH(CH₃)-phenyl | 455.3078 |

EXAMPLE 68

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

EXAMPLE 69

| Transdermal Patch Formulation | |
|---|---|
| Ingredient | Amount |
| Compound of formula I | 40 g |
| Silicone fluid | 45 g |
| Colloidal silicone dioxide | 2.5 g |

The silicone fluid and compound of structural formula I are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 cm$^2$ patches. For 100 Patches.

EXAMPLE 70

| Suppository | |
|---|---|
| Ingredient | Amount |
| Compound of structural formula I | 25 g |
| Polyethylene glycol 1000 | 1481 g |
| Polyethylene glycol 4000 | 494 g |

The polyethylene glycol 1000 and polyethylene glycol 4000 are mixed and melted. The compound of structural formula I is mixed into the molten mixture, poured into molds and allowed to cool. For 1000 suppositories.

EXAMPLE 71

| Injectable solution | |
|---|---|
| Ingredient | Amount |
| Compound of structural formula I | 5 g |
| Buffering agents | q.s. |
| Propylene glycol | 400 mg |
| Water for injection | 600 mL |

The compound of structural formula I and buffering agents are dissolved in the propylene glycol at about 50° C. The water for injection is then added with stirring and the resulting solution is filtered, filled into ampules, sealed and sterilized by autoclaving. For 1000 Ampules.

EXAMPLE 72

| Injectable solution | |
|---|---|
| Ingredient | Amount |
| Compound of structural formula I | 5 g |
| Buffering agents | q.s. |
| Magnesium sulfate heptahydrate | 100 mg |
| Water for injection | 880 mL |

The compound of structural formula I, magnesium sulfate heptahydrate and buffering agents are dissolved in the water for injection with stirring, and the resulting solution is filtered, filled into ampoules, sealed and sterilized by autoclaving. For 1000 Ampoules.

The following assays were used to characterize the activity of the tissue selective androgen receptor modulators of the present invention.

In Vitro and In Vivo Assays for Identification of Compounds With Sarm Activity 1. Hydroxylapatite-based Radioligand Displacement Assay of Compound Affinity for Endogenously Expressed AR Materials:
Binding Buffer: TEGM (10 mM Tris-HCl, 1 mM EDTA, 10% glycerol, 1 mM beta-mecaptoethanol, 10 mM Sodium Molybdate, pH 7.2)
50% HAP Slurry: Calbiochem Hydroxylapatite, Fast Flow, in 10 mM Tris, pH 8.0 and 1 mM EDTA.
Wash Buffer: 40 mM Tris, pH7.5, 100 mM KCl, 1 mM EDTA and 1 mM EGTA. 95% EtOH
Methyltrienolone, [17α-methyl-$^3$H], (R1881*); NEN NET590
Methyltrienolone (R1881), NEN NLP005 (dissolve in 95% EtOH)
Dihydrotestosterone (DHT) [1,2,4,5,6,7-$^3$H(N)] NEN NET453
Hydroxylapatite Fast Flow; Calbiochem Cat#391947
Molybdate=Molybdic Acid (Sigma, M1651)

| MDA-MB-453 cell culture media: RPMI 1640 (Gibco 11835-055) w/23.8 mM NaHCO$_3$, 2 mM L-glutamine | |
|---|---|
| In 500 mL of complete media | Final conc. |
| 10 mL (IM Hepes) | 20 mM |
| 5 mL (200 mM L-glu) | 4 mM |
| 0.5 mL (10 mg/mL human insulin) in 0.01 N HCl Calbiochem#407694-S) | 10 µg/mL |
| 50 mL FBS (Sigma F2442) | 10% |
| 1 mL (10 mg/mL Gentamicin Gibco#15710-072) | 20 µg/mL |

Cell Passaging:
Cells (Hall R. E., et al., *European Journal of Cancer*, 30A: 484–490 (1994)) are rinsed twice in PBS, phenol red-free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added to kill the trypsin. The cells are counted at this point, then diluted to the appropriate concentration and split into flasks or dishes for further culturing (Usually 1:3 to 1:6 dilution).

Preparation of MDA-MB-453 Cell Lysate

When the MDA cells are 70 to 85% confluent, they are detached as described above, and collected by centrifuging at 1000 g for 10 min at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of $10^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 μL of supernatant, the test compound can be prepared in 50 μL of the TEGM buffer.

Procedure for Multiple Compound Screening:

1×TEGM buffer is prepared, and the isotope-containing assay mixture is prepared in the following order: EtOH (2% final concentration in reaction), $^3$H-R1881 or $^3$H-DHT (0.5 nM final Conc. in reaction) and 1×TEGM. [eg. For 100 samples, 200 μL (100×2) of EtOH+4.25 μL of 1:10 $^3$H-R1881 stock+2300 μL (100×23) 1×TEGM]. The compound is serially diluted, e.g., if starting final conc. is 1 μM, and the compound is in 25 μL of solution, for duplicate samples, 75 μL of 4×1 μM solution is made and 3 μL of 100 μM is added to 72 μL of buffer, and 1:5 serial dilution.

25 μL of $^3$H-R1881 trace and 25 μL compound solution are first mixed together, followed by addition of 50 μL receptor solution. The reaction is gently mixed, spun briefly at about 200 rpm and incubated at 4° C. overnight. 100 μL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard). The washing process transfers HAP pellet containing ligand-bound expressed receptor to Unifilter-96 GF/B filter plate (Packard). The HAP pellet on the filter plate is incubated with 50 μL of MICROSCINT (Packard) scintillint for 30 minutes before being counted on the TopCount microscintillation counter (Packard). $IC_{50}$s are calculated using R1881 as a reference. Tissue selective androgen receptor modulators of the present invention displayed $IC_{50}$ values of 1 micromolar or less.

2. MMP1 Promoter Suppression, Transient Transfection Assay (TRAMPS).

HepG2 cells are cultured in phenol red free MEM containing 10% charcoal-treated FCS at 37 C with 5% $CO_2$. For transfection, cells are plated at 10,000 cells/well in 96 well white, clear bottom plates. Twenty four hours later, cells are co-transfected with a MMP1 promoter-luciferase reporter construct and a rhesus monkey expression construct (50:1 ratio) using FuGENE6 transfection reagent, following the protocol recommended by manufacturer. The MMP1 promoter-luciferase reporter construct is generated by insertion of a human MMP1 promoter fragment (−179/+63) into pGL2 luciferase reporter construct (Promega) and a rhesus monkey AR expression construct is generated in a CMV-Tag2B expression vector (Stratagene). Cells are further cultured for 24 hours and then treated with test compounds in the presence of 100 nM phorbol-12-myristate-13-acetate (PMA), used to increase the basal activity of MMP1 promoter. The compounds are added at this point, at a range of 1000 nM to 0.03 nM, 10 dilutions, at a concentration on 10×, 1/10th volume (example: 10 microliters of ligand at 10× added to 100 microliters of media already in the well). Cells are further cultured for an additional 48 hours. Cells are then washed twice with PBS and lysed by adding 70 μL of Lysis Buffer (1×, Promega) to the wells. The luciferase activity is measured in a 96-well format using a 1450 Microbeta Jet (Perkin Elmer) luminometer. Activity of test compounds is presented as suppression of luciferase signal from the PMA-stimulated control levels. $EC_{50}$ and Emax values are reported. Tissue selective androgen receptor modulators of the present invention activate repression typically with sub-micromolar $EC_{50}$ values and Emax values greater than about 50%.

References:
a. Newberry E P, Willis D, Latifi T, Boudreaux J M, Towler D A, "Fibroblast growth factor receptor signaling activates the human interstitial collagenase promoter via the bipartite Ets-AP1 element," *Mol. Endocrinol.* 11: 1129–44 (1997).
b. Schneikert J, Peterziel H, Defossez P A, Klocker H, Launoit Y, Cato A C, "Androgen receptor-Ets protein interaction is a novel mechanism for steroid hormone-mediated down-modulation of matrix metalloproteinase expression," *J. Biol. Chem.* 271: 23907–23913 (1996).

3. A Mammalian Two-Hybrid Assay for the Ligand-Induced Interaction of N-Terminus and C-Terminus Domains of the Androgen Receptor (Agonist Mode)

This assay assesses the ability of AR agonists to induce the interaction between the N-terminal domain (NTD) and C-terminal domain (CTD) of rhAR that reflects the in vivo virilizing potential mediated by activated androgen receptors. The interaction of NTD and CTD of rhAR is quantified as ligand induced association between a Gal4DBD-rh-ARCTD fusion protein and a VP16-rhARNTD fusion protein as a mammalian two-hybrid assay in CV-1 monkey kidney cells.

The day before transfection, CV-1 cells are trypsinized and counted, and then plated at 20,000 cells/well in 96-well plates or larger plates (scaled up accordingly) in DMEM+ 10% FCS. The next morning, CV-1 cells are cotransfected with pCBB1 (Gal4DBD-rhARLBD fusion construct expressed under the SV40 early promoter), pCBB2 (VP16-rhAR NTD fusion construct expressed under the SV40 early promoter) and pFR (Gal4 responsive luciferase reporter, Promega) using LIPOFECTAMINE PLUS reagent (GIBCO-BRL) following the procedure recommended by the vendor. Briefly, DNA admixture of 0.05 μg pCBB1, 0.05 μg pCBB2 and 0.1 μg of pFR is mixed in 3.4 μL OPTI-MEM (GIBCO-BRL) mixed with "PLUS Reagent" (1.6 μL, GIBCO-BRL) and incubated at room temperature (RT) for 15 min to form the pre-complexed DNA.

For each well, 0.4 μL LIPOFECTAMINE Reagent (GIBCO-BRL) is diluted into 4.6 μL OPTI-MEM in a second tube and mixed to form the diluted LIPO-FECTAMINE Reagent. The pre-complexed DNA (above) and the diluted LIPOFECTAMINE Reagent (above) are combined, mixed and incubated for 15 min at RT. The medium on the cells is replaced with 40 μL/well OPTI-MEM, and 10 μL DNA-lipid complexes are added to each well. The complexes are mixed into the medium gently and incubated at 37° C. at 5% $CO_2$ for 5h. Following incubation, 200 μL/well D-MEM and 13% charcoal-stripped FCS are added, followed by incubation at 37° C. at 5% $CO_2$. After 24 hours, the test compounds are added at the desired concentration(s) (1 nM–10 μM). Forty eight hours later, luciferase activity is measured using LUC-Screen system (TROPIX) following the manufacturer's protocol. The assay is conducted directly in the wells by sequential addition of 50 μL each of assay solution 1 followed by assay solution 2. After incubation for 40 minutes at room temperature, luminescence is directly measured with 2–5 second integration.

Activity of test compounds is calculated as the $E_{max}$ relative to the activity obtained with 3 nM R1881. Typical tissue-selective androgen receptor modulators of the present invention display weak or no agonist activity in this assay with less than 50% agonist activity at 10 micromolar.

Reference:
He B, Kemppainen J A, Voegel J J, Gronemeyer H, Wilson E M, "Activation function in the human androgen receptor ligand binding domain mediates inter-domain communication with the NH(2)-terminal domain," *J. Biol. Chem.* 274: 37219–37225 (1999).

4. A Mammalian Two-Hybrid Assay for Inhibition of Interaction between N-Terminus and C-Terminus Domains of Androgen Receptor (Antagonist Mode)

This assay assesses the ability of test compounds to antagonize the stimulatory effects of R1881 on the interaction between NTD and CTD of rhAR in a mammalian two-hybrid assay in CV-1 cells as described above.

Forty eight hours after transfection, CV-1 cells are treated with test compounds, typically at 10 μM, 3.3 μM, 1 μM, 0.33 μM, 100 nM, 33 nM, 10 nM, 3.3 nM and 1 nM final concentrations. After incubation at 37° C. at 5% $CO_2$ for 10–30 minutes, an AR agonist methyltrienolone (R1881) is added to a final concentration of 0.3 nM and incubated at 37° C. Forty-eight hours later, luciferase activity is measured using LUC-Screen system (TROPIX) following the protocol recommended by the manufacturer. The ability of test compounds to antagonize the action of R1881 is calculated as the relative luminescence compared to the value with 0.3 nM R1881 alone.

SARM compounds of the present invention typically displayed antagonist activity in the present assay with $IC_{50}$ values less than 1 micromolar.

5. Trans-Activation Modulation of Androgen Receptor (TAMAR)

This assay assesses the ability of test compounds to control transcription from the MMTV-LUC reporter gene in MDA-MB-453 cells, a human breast cancer cell line that naturally expresses the human AR. The assay measures induction of a modified MMTV LTR/promoter linked to the LUC reporter gene.

20,000 to 30,000 cells/well are plated in a white, clear-bottom 96-well plate in "Exponential Growth Medium" which consists of phenol red-free RPMI 1640 containing 10% FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media, and then gently mixed with the Fugene/DNA cocktail mix and plated onto the 96-well plate. All the wells receive 200 μl of medium+lipid/DNA complex and are then incubated at 37° C. overnight. The transfection cocktail consists of serum-free Optimem, Fugene6 reagent and DNA. The manufacturer's (Roche Biochemical) protocol for cocktail setup is followed. The lipid (μl) to DNA (μg) ratio is approximately 3:2 and the incubation time is 20 min at room temperature. Sixteen to 24 hrs after transfection, the cells are treated with test compounds such that the final DMSO (vehicle) concentration is <3%. The cells are exposed to the test compounds for 48 hrs. After 48 hrs, the cells are lysed by a Promega cell culture lysis buffer for 30–60 min and then the luciferase activity in the extracts is assayed in the 96-well format luminometer.

Activity of test compounds is calculated as the $E_{max}$ relative to the activity obtained with 100 nM R1881.

References:
a. R. E. Hall, et al., "MDA-MB-453, an androgen-responsive human breast carcinoma cell line with high androgen receptor expression," *Eur. J. Cancer*, 30A: 484–490 (1994).
b. R. E. Hall, et al., "Regulation of androgen receptor gene expression by steroids and retinoic acid in human breast-cancer cells," *Int. J. Cancer.*, 52: 778–784 (1992).

6. In Vivo Prostate Assay

Male Sprague-Dawley rats aged 9–10 weeks, the earliest age of sexual maturity, are used in prevention mode. The goal is to measure the degree to which androgen-like compounds delay the rapid deterioration (~–85%) of the ventral prostate gland and seminal vesicles that occurs during a seven day period after removal of the testes (orchiectomy [ORX]).

Rats are orchiectomized (ORX). Each rat is weighed, then anesthetized by isoflurane gas that is maintained to effect. A 1.5 cm anteroposterior incision is made in the scrotum. The right testicle is exteriorized. The spermatic artery and vas deferens are ligated with 4.0 silk 0.5 cm proximal to the testicle. The testicle is freed by one cut of a small surgical scissors distal to the ligation site. The tissue stump is returned to the scrotum. The same is repeated for the left testicle. When both stumps are returned to the scrotum, the scrotum and overlying skin are sutured closed with 4.0 silk. For Sham-ORX, all procedures excepting ligation and scissors cutting are completed. The rats fully recover consciousness and full mobility within 10–15 minutes.

A dose of test compound is administered subcutaneously or orally to the rat immediately after the surgical incision is sutured. Treatment continues for an additional six consecutive days.

Necropsy and Endpoints:

The rat is first weighed, then anesthetized in a $CO_2$ chamber until near death. Approximately 5 ml whole blood is obtained by cardiac puncture. The rat is then examined for certain signs of death and completeness of ORX. Next, the ventral portion of the prostate gland is located and blunt dissected free in a highly stylized fashion. The ventral prostate is blotted dry for 3–5 seconds and then weighed (VPW). Finally, the seminal vesicle is located and dissected free. The ventral seminal vesicle is blotted dry for 3–5 seconds and then weighed (SVWT).

Primary data for this assay are the weights of the ventral prostate and seminal vesicle. Secondary data include serum LH (luteinizing hormone) and FSH (follicle stimulating hormone), and possible serum markers of bone formation and virilization. Data are analyzed by ANOVA plus Fisher PLSD post-hoc test to identify intergroup differences. The extent to which test compounds inhibit ORX-induced loss of VPW and SVWT is assessed.

7. In Vivo Bone Formation Assay:

Female Sprague-Dawley rats aged 7–10 months are used in treatment mode to simulate adult human females. The rats have been ovariectomized (OVX) 75–180 days previously, to cause bone loss and simulate estrogen deficient, osteopenic adult human females. Pre-treatment with a low dose of a powerful anti-resorptive, alendronate (0.0028 mpk SC, 2x/wk) is begun on Day 0. On Day 15, treatment with test compound is started. Test compound treatment occurs on Days 15–31 with necropsy on Day 32. The goal is to measure the extent to which androgen-like compounds increase the amount of bone formation, shown by increased fluorochrome labeling, at the periosteal surface.

In a typical assay, nine groups of seven rats each are studied.

On Days 19 and 29 (fifth and fifteenth days of treatment), a single subcutaneous injection of calcein (8 mg/kg) is given to each rat.

Necropsy and Endpoints:

The rat is first weighed, then anesthetized in a $CO_2$ chamber until near death. Approximately 5 mL whole blood is obtained by cardiac puncture. The rat is then examined for certain signs of death and completeness of OVX. First, the uterus is located, blunt dissected free in a highly stylized fashion, blotted dry for 3–5 seconds and then weighed (UW). The uterus is placed in 10% neutral-buffered formalin. Next, the right leg is disarticulated at the hip. The femur and tibia are separated at the knee, substantially defleshed, and then placed in 70% ethanol.

A 1-cm segment of the central right femur, with the femoral proximal-distal midpoint ats center, is placed in a scintillation vial and dehydrated and defatted in graded alcohols and acetone, then introduced to solutions with increasing concentrations of methyl methacrylate. It is embedded in a mixture of 90% methyl methacrylate:10% dibutyl phthalate, that is allowed to polymerize over a 48–72 hr period. The bottle is cracked and the plastic block is trimmed into a shape that conveniently fits the vice-like specimen holder of a Leica 1600 Saw Microtome, with the long axis of the bone prepared for cross-sectioning. Three cross-sections of 85 μm thickness are prepared and mounted on glass slides. One section from each rat that approximates the midpoint of the bone is selected and blind-coded. The periosteal surface of each section is assessed for total periosteal surface, single fluorochrome label, double fluorochrome label, and interlabel distance.

Primary data for this assay are the percentage of periosteal surface bearing double label and the mineral apposition rate (interlabel distance(μm)/10 d), semi-independent markers of bone formation. Secondary data include uterus weight and histologic features. Tertiary endpoints may include serum markers of bone formation and virilization. Data are analyzed by ANOVA plus Fisher PLSD post-hoc test to identify intergroup differences. The extent to which test compounds increase bone formation endpoint are assessed.

While the foregoing specification teaches the principles of the present invention, with examples provided for the purpose of illustration, it is understood that the practice of the invention encompasses all of the usual variations, adoptions, or modifications, as being within the scope of the following claims and their equivalents.

What is claimed is:
1. A compound of structural formula I:

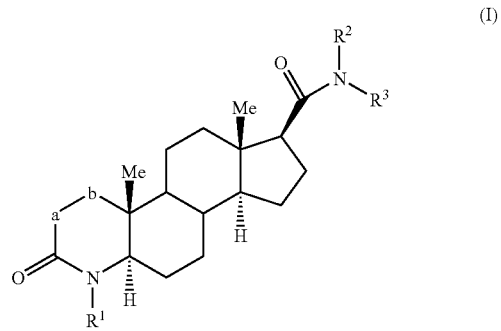

or a pharmaceutically acceptable salt or an enantiomer thereof; wherein n is 0, 1 or 2;
a-b represents CF=CH, CHFCH$_2$, or CF$_2$CH$_2$;
$R^1$ is hydrogen, hydroxymethyl, or $C_{1-3}$ alkyl, wherein alkyl is unsubstituted or substituted with one to seven fluorine atoms;
$R^2$ is hydrogen or $C_{1-4}$ alkyl;
$R^3$ is selected from
(CH$_2$)$_n$-cycloheteroalkyl, and
(CH$_2$)$_n$-aryl, wherein aryl is selected from
(1) phenyl,
(2) naphthyl,
(3) benzimidazolyl, or imidazopyridin
(4) benzofuranyl,
(5) benzothiophenyl,
(6) benzoxazolyl,
(7) benzothiazolyl,
(8) benzodihydrofuranyl,
(9) 1,3-benzodioxolyl,
(10) 2,3-dihydro-1,4-benzodioxinyl,
(11) indolyl,
(12) quinolyl,
(13) isoquinolyl,
(14) furanyl,
(15) thienyl,
(16) imidazolyl,
(17) oxazolyl,
(18) thiazolyl,
(19) isoxazolyl,
(20) isothiazolyl,
(21) pyrazolyl,
(22) pyrrolyl,
(23) pyridyl,
(24) pyrimidyl,
(25) pyrazinyl,
(26) thiadiazolyl,
(27) oxadiazolyl,
(28) triazolyl,
(29) tetrazolyl, and
(30) indanyl;
wherein the alkyl group or the cycloheteroalkyl group is unsubstituted or substituted with one to three substituents independently selected from halogen, hydroxy, and $C_{1-4}$ alkoxy; the aryl group as defined in items (1) to (30) is unsubstituted or substituted with one to three groups independently selected from halogen, phenyl, $C_{1-8}$ alkyl, $C_{3-8}$ cycloalkyl, $C_{3-8}$ cycloheteroalkyl, phenyl-$C_{1-6}$ alkyl, amino-$C_{0-6}$ alkyl, $C_{1-6}$ alkylamino-$C_{0-6}$ alkyl, (C$_{1-6}$ alkyl)$_2$amino-C$_{0-6}$ alkyl, phenyl-C$_{0-6}$ alkylamino-C$_{0-6}$ alkyl, (phenyl-C$_{0-6}$ alkyl)2amino-C$_{0-6}$ alkyl, C$_{1-6}$ alkylthio, phenyl-C$_{0-6}$ alkylthio, C$_{1-6}$ alkylsulfinyl, phenyl-C$_{0-6}$ alkylsulfinyl, C$_{1-6}$ alkylsulfonyl, phenyl-C$_{0-6}$ alkylsulfonyl, C$_{1-6}$ alkoxy-C$_{0-6}$ alkyl, phenyl-C$_{0-6}$ alkoxy-C$_{0-6}$ alkyl, hydroxycarbonyl-C$_{0-6}$ alkyl, C$_{1-6}$ alkoxycarbonyl-C$_{0-6}$ alkyl, phenyl-C$_{0-6}$ alkoxycarbonyl-C$_{0-6}$ alkyl, hydroxycarbonyl-C$_{1-6}$ alkyloxy, hydroxy-C$_{0-6}$ alkyl, cyano, nitro, perfluoro-C$_{1-4}$ alkyl, perfluoro-C$_{1-4}$ alkoxy, oxo, C$_{1-6}$ alkylcarbonyloxy, phenyl-C$_{0-6}$ alkylcarbonyloxy, C$_{1-6}$ alkylcarbonylamino, phenyl-C$_{0-6}$ alkylcarbonylamino, C$_{1-6}$ alkylsulfonylamino, phenyl-C$_{0-6}$ alkylsulfonylamino, C$_{1-6}$ alkoxycarbonylamino, phenyl-C$_{0-6}$ alkoxycarbonylamino, C$_{1-6}$ alkylaminocarbonylamino, phenyl-C$_{0-6}$ alkylaminocarbonylamino, (C$_{1-6}$ alkyl)$_2$ aminocarbonylamino, (phenyl-C$_{0-6}$ alkyl)$_2$ aminocarbonylamino, (C$_{1-6}$ alkyl)$_2$ aminocarbonyloxy, and (phenyl-C$_{0-6}$ alkyl)$_2$ aminocarbonyloxy; and wherein any methylene (CH$_2$) carbon atom in (CH$_2$)$_n$ is unsubstituted or substituted with one to two groups independently selected from halogen, hydroxy, and C$_{1-4}$ alkyl; or two substituents when on the same methylene (CH$_2$) group are taken together with the carbon atom to which they are attached to form a cyclopropyl group;

or R$^2$ and R$^3$ together form a 5- or 6-membered saturated ring fused with a 5- or 6-membered aromatic ring system having 0, 1, or 2 heteroatoms selected from the N, O, and S.

2. The compound of claim 1 wherein R$^1$ is hydrogen or methyl.

3. A compound of structural formula I:

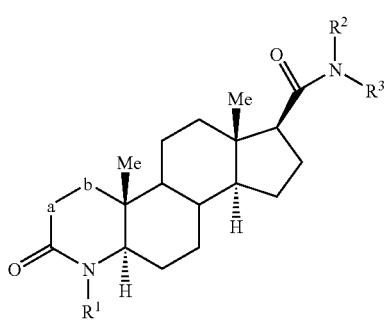

(I)

or a pharmaceutically acceptable salt or an enantiomer thereof; wherein
n is 0, 1 or 2;
a-b represents CF=CH, CHFCH$_2$, or CF$_2$CH$_2$;
R$^1$ is hydrogen, hydroxymethyl, or C$_{1-3}$ alkyl, wherein alkyl is unsubstituted or substituted with one to seven fluorine atoms;
R$^2$ is hydrogen or C$_{1-4}$ alkyl;
R$^3$ is
(CH$_2$)$_n$-aryl, wherein aryl is selected from
(1) phenyl,
(2) naphthyl,
(3) benzimidazolyl,
(4) imidazopyridinyl,
(5) benzofuranyl,
(6) benzothiophenyl,
(7) benzoxazolyl,
(8) benzothiazolyl,
(9) benzodihydrofuranyl,
(10) 1,3-benzodioxolyl,
(11) 2,3-dihydro-1,4-benzodioxinyl,
(12) indolyl,
(13) quinolyl,
(14) isoquinolyl,
(15) furanyl,
(16) thienyl,
(17) imidazolyl,
(18) oxazolyl,
(19) thiazolyl,
(20) isoxazolyl,
(21) isothiazolyl,
(22) pyrazolyl,
(23) pyrrolyl,
(24) pyridyl,
(25) pyrimidyl,
(26) pyrazinyl,
(27) thiadiazolyl,
(28) oxadiazolyl,
(29) triazolyl,
(30) tetrazolyl, and
(31) indanyl;
wherein the alkyl group or the cycloheteroalkyl group is unsubstituted or substituted with one to three substituents independently selected from halogen, hydroxy, and C$_{1-4}$ alkoxy; the aryl group as defined in items (1) to (30) is unsubstituted or substituted with one to three groups independently selected from halogen, phenyl, C$_{1-8}$ alkyl, C$_{3-8}$ cycloalkyl, C$_{3-8}$ cycloheteroalkyl, phenyl-C$_{1-6}$ alkyl, amino-C$_{0-6}$ alkyl, C$_{1-6}$ alkylamino-C$_{0-6}$ alkyl, (C$_{1-6}$ alkyl)$_2$amino-C$_{0-6}$ alkyl, phenyl-C$_{0-6}$ alkylamino-C$_{0-6}$ alkyl, (phenyl-C$_{0-6}$ alkyl)$_2$amino-C$_{0-6}$ alkyl, C$_{1-6}$ alkylthio, phenyl-C$_{0-6}$ alkylthio, C$_{1-6}$ alkylsulfinyl, phenyl-C$_{0-6}$ alkylsulfinyl, C$_{1-6}$ alkylsulfonyl, phenyl-C$_{0-6}$ alkylsulfonyl, C$_{1-6}$ alkoxy-C$_{1-6}$ alkyl, phenyl-C$_{0-6}$ alkoxy-C$_{0-6}$ alkyl, hydroxycarbonyl-C$_{0-6}$ alkyl, C$_{1-6}$ alkoxycarbonyl-C$_{0-6}$ alkyl, phenyl-C$_{0-6}$ alkoxycarbonyl-C$_{0-6}$ alkyl, hydroxycarbonyl-C$_{1-6}$ alkyloxy, hydroxy-C$_{0-6}$ alkyl, cyano, nitro, perfluoro-C$_{1-4}$ alkyl, perfluoro-C$_{1-4}$ alkoxy, oxo, C$_{1-6}$ alkylcarbonyloxy, phenyl-C$_{0-6}$ alkylcarbonyloxy, C$_{1-6}$ alkylcarbonylamino, phenyl-C$_{0-6}$ alkylcarbonylamino, C$_{1-6}$ alkylsulfonylamino, phenyl-C$_{0-6}$ alkylsulfonylamino, C$_{1-6}$ alkoxycarbonylamino, phenyl-C$_{0-6}$ alkoxycarbonylamino, C$_{1-6}$ alkylaminocarbonylamino, phenyl-C$_{0-6}$ alkylaminocarbonylamino, (C$_{1-6}$ alkyl)$_2$ aminocarbonylamino, (phenyl-C$_{0-6}$ alkyl)$_2$ aminocarbonylamino, (C$_{1-6}$ alkyl)$_2$ aminocarbonyloxy, and (phenyl-C$_{0-6}$ alkyl)$_2$ aminocarbonyloxy; and wherein any methylene (CH$_2$) carbon atom in (CH$_2$)$_n$ is unsubstituted or substituted with one to two groups independently selected from halogen, hydroxy, and C$_{1-4}$ alkyl; or two substituents when on the same methylene (CH$_2$) group are taken together with the carbon atom to which they are attached to form a cyclopropyl group;

or R$^2$ and R$^3$ together form a 5- or 6-membered saturated ring fused with a 5- or 6-membered aromatic ring system having 0, 1, or 2 heteroatoms selected from the N, O, and S.

4. The compound of claim 3, wherein R$^1$ is hydrogen or methyl.

5. The compound of claim 1 wherein a-b represents CF=CH.

6. The compound of claim 1 wherein a-b represents CHFCH$_2$.

7. The compound of claim 1 wherein R$^2$ is hydrogen and R$^3$ is (CH$_2$)$_n$-aryl.

8. The compound of claim 7 wherein n is 0 or 1.

9. The compound of claim 1 wherein $R^1$ is methyl, a-b represents CF=CH, $R^2$ is hydrogen, and $R^3$ is $(CH_2)_n$-aryl.

10. The compound of claim 9 wherein n is 0 or 1.

11. The compound of claim 1 wherein $R^1$ is methyl, a-b represents $CHFCH_2$, $R^2$ is hydrogen, and $R^3$ is $(CH_2)_n$-aryl 12. The compound of claim 11 wherein n is 0 or 1.

13. The compound of claim 1 wherein $R^1$ is methyl, a-b represents CF=CH, $R^2$ is hydrogen, and $R^3$ is $(CH_2)_n$-cycloheteroalkyl.

14. The compound of claim 13, wherein n is 0 or 1.

15. The compound of claim 1 wherein $R^1$ is methyl, a-b represents $CHFCH_2$, $R^2$ is hydrogen, and $R^3$ is $(CH_2)_n$-cycloheteroalkyl.

16. The compound of claim 15, wherein n is 0 or 1.

17. The compound of claim 2 chosen from:
N-(2-fluorophenylmethyl)-2-fluoro-4-methyl-3-oxo-4-aza-5α-androst-1-en-17β-carboxamide;
N-(3-fluorophenylmethyl)-2-fluoro-4-methyl-3-oxo-4-aza-5α-androst-1-en-17β-carboxamide;
N-(2-trifluoromethylphenyl)-2-fluoro-4-methyl-3-oxo-4-aza-5α-androst-1-en-17β-carboxamide;
N-(2-chlorophenyl)-2-fluoro-4-methyl-3-oxo-4-aza-5α-androst-1-en-17β-carboxamide;
N-(4-methoxyphenyl)-2-fluoro-4-methyl-3-oxo-4-aza-5α-androst-1-en-17β-carboxamide;
N-(3-methoxyphenyl)-2-fluoro-4-methyl-3-oxo-4-aza-5α-androst-1-en-17β-carboxamide;
N-(2-methylphenyl)-2-fluoro-4-methyl-3-oxo-4-aza-5α-androst-1-en-17β-carboxamide;
N-(3-methylphenyl)-2-fluoro-4-methyl-3-oxo-4-aza-5α-androst-1-en-17β-carboxamide;
N-(2-fluorophenyl)-2-fluoro-4-methyl-3-oxo-4-aza-5α-androst-1-en-17β-carboxamide;
N-(3-fluorophenyl)-2-fluoro-4-methyl-3-oxo-4-aza-5α-androst-1-en-17β-carboxamide;
N-(4-fluorophenyl)-2-fluoro-4-methyl-3-oxo-4-aza-5α-androst-1-en-17β-carboxamide;
N-(4-chloro-2-fluorophenyl)-2-fluoro-4-methyl-3-oxo-4-aza-5α-androst-1-en-17β-carboxamide;
N-(2,4-difluorophenyl)-2-fluoro-4-methyl-3-oxo-4-aza-5α-androst-1-en-17β-carboxamide;
N-(α-methylphenylmethyl)-2-fluoro-4-methyl-3-oxo-4-aza-5α-androst-1-en-17β-carboxamide;
N-(phenyl)-2-fluoro-4-methyl-3-oxo-4-aza-5α-androst-1-en-17β-carboxamide;
N-(4-chloro-2-trifluoromethylphenyl)-2-fluoro-4-methyl-3-oxo-4-aza-5α-androst-1-en-17β-carboxamide;
N-(5-methylpyridin-2-yl)-2-fluoro-4-methyl-3-oxo-4-aza-5α-androst-1-en-17β-carboxamide;
N-(thiophen-2-ylmethyl)-2-fluoro-4-methyl-3-oxo-4-aza-5α-androst-1-en-17β-carboxamide;
N-(thiophen-3-ylmethyl)-2-fluoro-4-methyl-3-oxo-4-aza-5α-androst-1-en-17β-carboxamide;
N-(2-trifluoromethylphenylmethyl)-2-fluoro-4-methyl-3-oxo-4-aza-5α-androst-1-en-17β-carboxamide;
N-(benzimidazol-2-ylmethyl)-2-fluoro-4-methyl-3-oxo-4-aza-5α-androst-1-en-17β-carboxamide;
N-(1-methylbenzimidazol-2-ylmethyl)-2-fluoro-4-methyl-3-oxo-4-aza-5α-androst-1-en-17β-carboxamide;
N-(1-methyl-5-trifluoromethylbenzimidazol-2-ylmethyl)-2-fluoro-4-methyl-3-oxo-4-aza-5α-androst-1-en-17β-carboxamide;
N-(5-chlorobenzimidazol-2-ylmethyl)-2-fluoro-4-methyl-3-oxo-4-aza-5α-androst-1-en-17β-carboxamide;
N-(5-methoxybenzimidazol-2-ylmethyl)-2-fluoro-4-methyl-3-oxo-4-aza-5α-androst-1-en-17β-carboxamide;
N-(benzthiazol-2-ylmethyl)-2-fluoro-4-methyl-3-oxo-4-aza-5α-androst-1-en-17β-carboxamide;
N-(2,3-dihydro-1,4-benzodioxin-2-ylmethyl)-2-fluoro-4-methyl-3-oxo-4-aza-5α-androst-1-en-17β-carboxamide;
N-(thiazol-2-ylmethyl)-2-fluoro-4-methyl-3-oxo-4-aza-5α-androst-1-en-17β-carboxamide;
N-(4-methylthiazol-2-ylmethyl)-2-fluoro-4-methyl-3-oxo-4-aza-5α-androst-1-en-17β-carboxamide;
N-(thiazol-4-ylmethyl)-2-fluoro-4-methyl-3-oxo-4-aza-5α-androst-1-en-17β-carboxamide;
N-(1-methylimidazol-2-ylmethyl)-2-fluoro-4-methyl-3-oxo-4-aza-5α-androst-1-en-17β-carboxamide;
N-(tetrahydro-2H-pyran-2(S)-ylmethyl)-2-fluoro-4-methyl-3-oxo-4-aza-5α-androst-1-en-17β-carboxamide;
N-(tetrahydro-2H-pyran-2(R)-ylmethyl)-2-fluoro-4-methyl-3-oxo-4-aza-5α-androst-1-en-17β-carboxamide;
N-(2,3-dihydro-1,4-benzodioxin-2(R)-ylmethyl)-2-fluoro-4-methyl-3-oxo-4-aza-5α-androst-1-en-17β-carboxamide;
N-(2,3-dihydro-1,4-benzodioxin-2(S)-ylmethyl)-2-fluoro-4-methyl-3-oxo-4-aza-5α-androst-1-en-17β-carboxamide;
N-(tetrahydrofuran-2(S)-ylmethyl)-2-fluoro-4-methyl-3-oxo-4-aza-5α-androst-1-en-17β-carboxamide;
N-(tetrahydrofuran-2(R)-ylmethyl)-2-fluoro-4-methyl-3-oxo-4-aza-5α-androst-1-en-17β-carboxamide;
N-(3H-imidazo[4,5-b]pyridin-2-ylmethyl)-2-fluoro-4-methyl-3-oxo-4-aza-5α-androst-1-en-17β-carboxamide;
N-(2-fluorophenylmethyl)-2α-fluoro-4-methyl-3-oxo-4-aza-5α-androstan-17β-carboxamide;
N-(2-trifluoromethylphenylmethyl)-2α-fluoro-4-methyl-3-oxo-4-aza-5α-androstan-17β-carboxamide;
N-(3-methoxyphenyl)-2α-fluoro-4-methyl-3-oxo-4-aza-5α-androstan-17β-carboxamide;
N-(4-methoxyphenyl)-2α-fluoro-4-methyl-3-oxo-4-aza-5α-androstan-17β-carboxamide;
N-(2-trifluoromethylphenyl)-2α-fluoro-4-methyl-3-oxo-4-aza-5α-androstan-17β-carboxamide;
N-(2-chlorophenyl)-2α-fluoro-4-methyl-3-oxo-4-aza-5α-androstan-17β-carboxamide;
N-(2-fluorophenylmethyl)-2α-fluoro-4-methyl-3-oxo-4-aza-5α-androstan-17β-carboxamide;
N-(benzimidazol-2-ylmethyl)-2α-fluoro-4-methyl-3-oxo-4-aza-5α-androstan-17β-carboxamide;
N-(1-methylbenzimidazol-2-ylmethyl)-2α-fluoro-4-methyl-3-oxo-4-aza-5α-androstan-17β-carboxamide;
N-(thiazol-2-ylmethyl)-2α-fluoro-4-methyl-3-oxo-4-aza-5α-androstan-17β-carboxamide;
N-(furan-2-ylmethyl)-2α-fluoro-4-methyl-3-oxo-4-aza-5α-androstan-17β-carboxamide; and
N-(thiophen-2-ylmethyl)-2α-fluoro-4-methyl-3-oxo-4-aza-5α-androstan-17β-carboxamide;
pharmaceutically acceptable salts and enantiomers thereof.

18. The compound of claim 17 chosen from:
N-(2-fluorophenylmethyl)-2-fluoro-4-methyl-3-oxo-4-aza-5α-androst-1-en-17β-carboxamide;
N-(3-fluorophenylmethyl)-2-fluoro-4-methyl-3-oxo-4-aza-5α-androst-1-en-17β-carboxamide;
N-(5-chlorobenzimidazol-2-ylmethyl)-2-fluoro-4-methyl-3-oxo-4-aza-5α-androst-1-en-17β-carboxamide;
N-(5-methoxybenzimidazol-2-ylmethyl)-2-fluoro-4-methyl-3-oxo-4-aza-5α-androst-1-en-17β-carboxamide;
N-(benzthiazol-2-ylmethyl)-2-fluoro-4-methyl-3-oxo-4-aza-5α-androst-1-en-17β-carboxamide;

N-(tetrahydro-2H-pyran-2(S)-ylmethyl)-2-fluoro-4-methyl-3-oxo-4-aza-5α-androst-1-en-17β-carboxamide;
N-(tetrahydro-2H-pyran-2(R)-ylmethyl)-2-fluoro-4-methyl-3-oxo-4-aza-5α-androst-1-en-17β-carboxamide;
N-(2,3-dihydro-1,4-benzodioxin-2(R)-ylmethyl)-2-fluoro-4-methyl-3-oxo-4-aza-5α-androst-1-en-17β-carboxamide;
N-(2,3-dihydro-1,4-benzodioxin-2(S)-ylmethyl)-2-fluoro-4-methyl-3-oxo-4-aza-5α-androst-1-en-17β-carboxamide;
N-(tetrahydrofuran-2(S)-ylmethyl)-2-fluoro-4-methyl-3-oxo-4-aza-5α-androst-1-en-17β-carboxamide;
N-(tetrahydrofuran-2(R)-ylmethyl)-2-fluoro-4-methyl-3-oxo-4-aza-5α-androst-1-en-17β-carboxamide;
N-(3H-imidazo[4,5-b]pyridin-2-ylmethyl)-2-fluoro-4-methyl-3-oxo-4-aza-5α-androst-1-en-17β-carboxamide;
N-(2-fluorophenylmethyl)-2α-fluoro-4-methyl-3-oxo-4-aza-5α-androstan-17β-carboxamide;
N-(thiazol-2-ylmethyl)-2α-fluoro-4-methyl-3-oxo-4-aza-5α-androstan-17β-carboxamide;
N-(furan-2-ylmethyl)-2α-fluoro-4-methyl-3-oxo-4-aza-5α-androstan-17β-carboxamide; and
N-(thiophen-2-ylmethyl)-2α-fluoro-4-methyl-3-oxo-4-aza-5α-androstan-17β-carboxamide;
pharmaceutically acceptable salts and enantiomers thereof.

19. The compound of claim 18 chosen from:
N-(tetrahydro-2H-pyran-2(S)-ylmethyl)-2-fluoro-4-methyl-3-oxo-4-aza-5α-androst-1-en-17β-carboxamide;
N-(tetrahydro-2H-pyran-2(R)-ylmethyl)-2-fluoro-4-methyl-3-oxo-4-aza-5α-androst-1-en-17β-carboxamide;
N-(2,3-dihydro-1,4-benzodioxin-2(R)-ylmethyl)-2-fluoro-4-methyl-3-oxo-4-aza-5α-androst-1-en-17β-carboxamide;
N-(2,3-dihydro-1,4-benzodioxin-2(S)-ylmethyl)-2-fluoro-4-methyl-3-oxo-4-aza-5α-androst-1-en-17β-carboxamide;
N-(tetrahydrofuran-2(S)-ylmethyl)-2-fluoro-4-methyl-3-oxo-4-aza-5α-androst-1-en-17β-carboxamide;
N-(tetrahydrofuran-2(R)-ylmethyl)-2-fluoro-4-methyl-3-oxo-4-aza-5α-androst-1-en-17β-carboxamide;
N-(3H-imidazo[4,5-b]pyridin-2-ylmethyl)-2-fluoro-4-methyl-3-oxo-4-aza-5α-androst-1-en-17β-carboxamide;
pharmaceutically acceptable salts and enantiomers thereof.

20. The compound of claim 18 chosen from:
N-(2-fluorophenylmethyl)-2-fluoro-4-methyl-3-oxo-4-aza-5α-androst-1-en-17β-carboxamide;
N-(3-fluorophenylmethyl)-2-fluoro-4-methyl-3-oxo-4-aza-5α-androst-1-en-17β-carboxamide;
N-(5-chlorobenzimidazol-2-ylmethyl)-2-fluoro-4-methyl-3-oxo-4-aza-5α-androst-1-en-17β-carboxamide;
N-(5-methoxybenzimidazol-2-ylmethyl)-2-fluoro-4-methyl-3-oxo-4-aza-5α-androst-1-en-17β-carboxamide;
N-(benzthiazol-2-ylmethyl)-2-fluoro-4-methyl-3-oxo-4-aza-5α-androst-1-en-17β-carboxamide;
N-(2-fluorophenylmethyl)-2α-fluoro-4-methyl-3-oxo-4-aza-5α-androstan-17β-carboxamide;
N-(thiazol-2-ylmethyl)-2α-fluoro-4-methyl-3-oxo-4-aza-5α-androstan-17β-carboxamide;
N-(furan-2-ylmethyl)-2α-fluoro-4-methyl-3-oxo-4-aza-5α-androstan-17β-carboxamide; and
N-(thiophen-2-ylmethyl)-2α-fluoro-4-methyl-3-oxo-4-aza-5α-androstan-17β-carboxamide;
pharmaceutically acceptable salts and enantiomers thereof.

21. A compound of claim 17, chosen from:
N-(2-fluorophenylmethyl)-2α-fluoro-4-methyl-3-oxo-4-aza-5α-androstan-17β-carboxamide,
N-(benzimidazol-2-ylmethyl)-2α-fluoro-4-methyl-3-oxo-4-aza-5α-androstan-17β-carboxamide,
N-(3H-imidazo[4,5-b]pyridin-2-ylmethyl)-2-fluoro-4-methyl-3-oxo-4-aza-5α-androst-1-en-17β-carboxamide,
pharmaceutically acceptable salts and enantiomers thereof.

22. A compound chosen from:
N-(2-fluorophenylmethyl)-2α-fluoro-4-methyl-3-oxo-4-aza-5α-androstan-17β-carboxamide,
pharmaceutically acceptable salts and enantiomers thereof.

23. A compound chosen from:
N-(benzimidazol-2-ylmethyl)-2α-fluoro-4-methyl-3-oxo-4-aza-5α-androstan-17β-carboxamide,
pharmaceutically acceptable salts and enantiomers thereof.

24. A compound of structural formula:

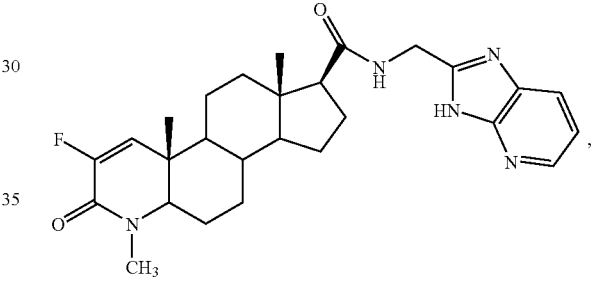

pharmaceutically acceptable salts and enantiomers thereof.

25. A compound of structural formula:

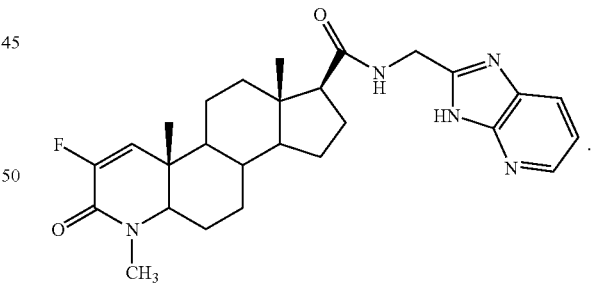

pharmaceutically acceptable salts and enantiomers thereof.

* * * * *